United States Patent
Pilgeram

(10) Patent No.: US 9,402,620 B2
(45) Date of Patent: Aug. 2, 2016

(54) KNOTLESS FILAMENTARY FIXATION DEVICES, ASSEMBLIES AND SYSTEMS AND METHODS OF ASSEMBLY AND USE

(71) Applicant: Howmedica Osteonics Corp., Mahwah, NJ (US)

(72) Inventor: Kyle Craig Pilgeram, San Jose, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 321 days.

(21) Appl. No.: 13/783,804

(22) Filed: Mar. 4, 2013

(65) Prior Publication Data
US 2014/0249577 A1   Sep. 4, 2014

(51) Int. Cl.
*A61B 17/04* (2006.01)

(52) U.S. Cl.
CPC ......... *A61B 17/0485* (2013.01); *A61B 17/0401* (2013.01); *A61B 2017/044* (2013.01); *A61B 2017/0406* (2013.01); *A61B 2017/0409* (2013.01); *A61B 2017/0458* (2013.01); *A61B 2017/0475* (2013.01)

(58) Field of Classification Search
CPC .................... A61B 25/10; A61B 2017/00557; A61B 17/0218; A61B 2017/22072; A61M 29/02; A61M 25/1002; A61M 25/1029; A61M 25/1027; A61M 2025/0175; A61M 25/104; A61M 25/04
USPC ........................ 606/228, 139, 232, 148, 216
See application file for complete search history.

(56) References Cited

U.S. PATENT DOCUMENTS

| | | |
|---|---|---|
| 749,624 A | 1/1904 | Mc Cullough |
| 1,308,798 A | 7/1919 | Masland |
| 1,624,530 A | 4/1927 | Caruso |
| 2,073,903 A | 3/1937 | O'Neil |
| 2,267,925 A | 12/1941 | Johnston |
| 2,382,019 A | 8/1945 | Miller |
| 2,494,229 A | 1/1950 | Collison |
| 2,515,365 A | 7/1950 | Zublin |
| 2,547,571 A | 4/1951 | Ettinger |
| 2,808,632 A | 10/1957 | Cline |
| 2,833,284 A | 5/1958 | Springer |
| 3,384,085 A | 5/1968 | Hall |

(Continued)

FOREIGN PATENT DOCUMENTS

| | | |
|---|---|---|
| DE | 3131496 A1 | 2/1983 |
| DE | 4231101 A1 | 3/1994 |

(Continued)

OTHER PUBLICATIONS

BIOMET Sports Medicine: Micromax Flex Suture Anchor, (2008).

(Continued)

*Primary Examiner* — Katherine Rodjom
(74) *Attorney, Agent, or Firm* — Lerner, David, Littenberg, Krumholz & Mentlik, LLP

(57) ABSTRACT

In one embodiment, the present invention include a method of securing tissue using a filamentary construct, the method including the steps of passing a length of filament through or around tissue; implanting a filamentary sleeve, formed of filament, into tissue; and passing at least a portion of the length of filament at least partially through the filamentary sleeve to form a one-way cleat. The present invention also provides for various devices, systems, assemblies, kits and methods of use, assembly and manufacture thereof.

9 Claims, 20 Drawing Sheets

(56) References Cited

U.S. PATENT DOCUMENTS

| | | |
|---|---|---|
| 3,461,875 A | 8/1969 | Hall |
| 3,554,192 A | 1/1971 | Isberner |
| 3,580,256 A | 5/1971 | Wilkinson et al. |
| 3,608,095 A | 9/1971 | Barry |
| 3,659,597 A | 5/1972 | Wolfers |
| 3,750,671 A | 8/1973 | Hedrick |
| 3,810,456 A | 5/1974 | Karman |
| 3,845,772 A | 11/1974 | Smith |
| 3,867,932 A | 2/1975 | Huene |
| 3,892,232 A | 7/1975 | Neufeld |
| 3,976,079 A | 8/1976 | Samuels et al. |
| 4,265,231 A | 5/1981 | Scheller, Jr. et al. |
| 4,328,839 A | 5/1982 | Lyons et al. |
| 4,483,562 A | 11/1984 | Schoolman |
| 4,489,446 A | 12/1984 | Reed |
| 4,541,423 A | 9/1985 | Barber |
| 4,608,972 A | 9/1986 | Small |
| 4,611,515 A | 9/1986 | Marbourg, Jr. |
| 4,646,738 A | 3/1987 | Trott |
| 4,706,659 A | 11/1987 | Matthews et al. |
| 4,741,330 A | 5/1988 | Hayhurst |
| 4,748,872 A | 6/1988 | Brown |
| 4,751,922 A | 6/1988 | DiPietropolo |
| 4,781,182 A | 11/1988 | Purnell et al. |
| 4,823,780 A | 4/1989 | Odensten et al. |
| 4,863,471 A | 9/1989 | Mansat |
| 4,872,451 A | 10/1989 | Moore et al. |
| 4,946,462 A | 8/1990 | Watanabe |
| 5,002,546 A | 3/1991 | Romano |
| 5,021,059 A | 6/1991 | Kensey et al. |
| 5,030,219 A | 7/1991 | Matsen, III et al. |
| 5,037,422 A | 8/1991 | Hayhurst et al. |
| 5,037,423 A | 8/1991 | Kenna |
| 5,061,277 A | 10/1991 | Carpentier et al. |
| 5,064,431 A | 11/1991 | Gilbertson et al. |
| 5,122,134 A | 6/1992 | Borzone et al. |
| 5,123,914 A | 6/1992 | Cope |
| 5,133,720 A | 7/1992 | Greenberg |
| 5,139,520 A | 8/1992 | Rosenberg |
| 5,141,520 A | 8/1992 | Goble et al. |
| 5,163,940 A | 11/1992 | Bourque |
| 5,190,548 A | 3/1993 | Davis |
| 5,203,595 A | 4/1993 | Borzone et al. |
| 5,203,787 A | 4/1993 | Noblitt et al. |
| RE34,293 E | 6/1993 | Goble et al. |
| 5,234,435 A | 8/1993 | Seagrave, Jr. |
| 5,259,846 A | 11/1993 | Granger et al. |
| 5,269,785 A | 12/1993 | Bonutti |
| 5,269,809 A | 12/1993 | Hayhurst et al. |
| 5,300,077 A | 4/1994 | Howell |
| 5,314,429 A | 5/1994 | Goble |
| 5,320,115 A | 6/1994 | Kenna |
| 5,320,626 A | 6/1994 | Schmieding |
| 5,324,308 A | 6/1994 | Pierce |
| 5,350,383 A | 9/1994 | Schmieding et al. |
| RE34,762 E | 10/1994 | Goble et al. |
| 5,374,269 A | 12/1994 | Rosenberg |
| 5,385,567 A | 1/1995 | Goble |
| 5,391,170 A | 2/1995 | McGuire et al. |
| 5,391,171 A | 2/1995 | Schmieding |
| RE34,871 E | 3/1995 | McGuire et al. |
| 5,395,188 A | 3/1995 | Bailey et al. |
| 5,403,317 A | 4/1995 | Bonutti |
| 5,403,348 A | 4/1995 | Bonutti |
| 5,405,359 A | 4/1995 | Pierce |
| 5,409,494 A | 4/1995 | Morgan |
| 5,417,691 A | 5/1995 | Hayhurst |
| 5,423,860 A | 6/1995 | Lizardi et al. |
| 5,437,677 A | 8/1995 | Shearer et al. |
| 5,441,502 A | 8/1995 | Bartlett |
| 5,443,482 A | 8/1995 | Stone et al. |
| 5,458,604 A | 10/1995 | Schmieding |
| 5,464,407 A | 11/1995 | McGuire |
| 5,464,425 A | 11/1995 | Skiba |
| 5,464,426 A | 11/1995 | Bonutti |
| 5,466,243 A | 11/1995 | Schmieding et al. |
| 5,472,452 A | 12/1995 | Trott |
| 5,486,197 A | 1/1996 | Le et al. |
| 5,488,761 A | 2/1996 | Leone |
| 5,496,348 A | 3/1996 | Bonutti |
| 5,505,736 A | 4/1996 | Reimels et al. |
| 5,520,693 A | 5/1996 | McGuire et al. |
| 5,520,700 A | 5/1996 | Beyar et al. |
| 5,522,846 A | 6/1996 | Bonutti |
| 5,527,316 A | 6/1996 | Stone et al. |
| 5,527,343 A | 6/1996 | Bonutti |
| 5,529,580 A | 6/1996 | Kusunoki et al. |
| 5,531,759 A | 7/1996 | Kensey et al. |
| 5,534,012 A | 7/1996 | Bonutti |
| 5,540,703 A | 7/1996 | Barker, Jr. et al. |
| 5,545,178 A | 8/1996 | Kensey et al. |
| 5,548,862 A | 8/1996 | Curtis |
| 5,569,269 A | 10/1996 | Hart et al. |
| 5,569,306 A | 10/1996 | Thal |
| 5,570,706 A | 11/1996 | Howell |
| 5,571,111 A | 11/1996 | Aboczky |
| 5,573,542 A | 11/1996 | Stevens |
| 5,575,819 A | 11/1996 | Amis |
| 5,584,695 A | 12/1996 | Lal Sachdeva et al. |
| 5,584,835 A | 12/1996 | Greenfield |
| 5,601,557 A | 2/1997 | Hayhurst |
| 5,601,561 A | 2/1997 | Terry et al. |
| 5,618,314 A | 4/1997 | Harwin et al. |
| 5,645,545 A | 7/1997 | Bryant |
| 5,645,589 A | 7/1997 | Li |
| 5,647,874 A | 7/1997 | Hayhurst |
| 5,649,963 A | 7/1997 | McDevitt |
| 5,658,313 A | 8/1997 | Thal |
| 5,662,658 A | 9/1997 | Wenstrom, Jr. |
| 5,665,110 A | 9/1997 | Chervitz et al. |
| 5,665,111 A | 9/1997 | Ray et al. |
| 5,665,112 A | 9/1997 | Thal |
| 5,667,509 A | 9/1997 | Westin |
| 5,674,279 A | 10/1997 | Wright et al. |
| 5,681,320 A | 10/1997 | McGuire |
| 5,681,352 A | 10/1997 | Clancy, III et al. |
| 5,683,401 A | 11/1997 | Schmieding et al. |
| 5,683,418 A | 11/1997 | Luscombe et al. |
| 5,683,419 A | 11/1997 | Thal |
| 5,690,676 A | 11/1997 | DiPoto et al. |
| 5,690,677 A | 11/1997 | Schmieding et al. |
| 5,695,513 A | 12/1997 | Johnson et al. |
| 5,699,657 A | 12/1997 | Paulson |
| 5,709,708 A | 1/1998 | Thal |
| 5,713,905 A | 2/1998 | Goble et al. |
| 5,716,397 A | 2/1998 | Myers |
| 5,718,717 A | 2/1998 | Bonutti |
| 5,720,765 A | 2/1998 | Thal |
| 5,725,541 A | 3/1998 | Anspach, III et al. |
| 5,728,136 A | 3/1998 | Thal |
| 5,732,606 A | 3/1998 | Chiang |
| 5,733,306 A | 3/1998 | Bonutti |
| 5,733,307 A | 3/1998 | Dinsdale |
| 5,749,899 A | 5/1998 | Bardin et al. |
| 5,755,724 A | 5/1998 | Yoon |
| 5,755,731 A | 5/1998 | Grinberg |
| 5,766,221 A | 6/1998 | Benderev et al. |
| 5,782,862 A | 7/1998 | Bonutti |
| 5,782,864 A | 7/1998 | Lizardi |
| 5,782,866 A | 7/1998 | Wenstrom, Jr. |
| 5,797,918 A | 8/1998 | McGuire et al. |
| 5,810,825 A | 9/1998 | Huebner |
| 5,814,056 A | 9/1998 | Prosst et al. |
| 5,836,953 A | 11/1998 | Yoon |
| 5,851,208 A | 12/1998 | Trott |
| 5,885,294 A | 3/1999 | Pedlick et al. |
| 5,888,034 A | 3/1999 | Greenberg |
| 5,891,168 A | 4/1999 | Thal |
| 5,897,574 A | 4/1999 | Bonutti |
| 5,906,626 A | 5/1999 | Carrillo |
| 5,921,986 A | 7/1999 | Bonutti |
| 5,928,244 A | 7/1999 | Tovey et al. |
| 5,941,139 A | 8/1999 | Vodehnal |
| 5,948,002 A | 9/1999 | Bonutti |

(56) References Cited

U.S. PATENT DOCUMENTS

| | | |
|---|---|---|
| 5,951,559 A | 9/1999 | Burkhart |
| 5,968,078 A | 10/1999 | Grotz |
| 5,970,697 A | 10/1999 | Jacobs et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,993,451 A | 11/1999 | Burkhart |
| 5,997,541 A | 12/1999 | Schenk |
| 6,007,566 A | 12/1999 | Wenstrom, Jr. |
| 6,007,567 A | 12/1999 | Bonutti |
| 6,010,515 A | 1/2000 | Swain et al. |
| 6,010,525 A | 1/2000 | Bonutti et al. |
| 6,019,767 A | 2/2000 | Howell |
| 6,024,758 A | 2/2000 | Thal |
| 6,045,574 A | 4/2000 | Thal |
| 6,053,922 A | 4/2000 | Krause et al. |
| 6,068,642 A | 5/2000 | Johnson et al. |
| 6,077,292 A | 6/2000 | Bonutti |
| 6,083,522 A | 7/2000 | Chu et al. |
| 6,120,511 A | 9/2000 | Chan |
| 6,143,017 A | 11/2000 | Thal |
| 6,146,385 A | 11/2000 | Torrie et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,183,461 B1 | 2/2001 | Matsuura et al. |
| 6,187,011 B1 | 2/2001 | Torrie |
| 6,189,422 B1 | 2/2001 | Stihl |
| 6,210,415 B1 | 4/2001 | Bester |
| 6,224,608 B1 | 5/2001 | Ciccolella et al. |
| 6,245,081 B1 | 6/2001 | Bowman et al. |
| 6,254,604 B1 | 7/2001 | Howell |
| 6,306,138 B1 | 10/2001 | Clark et al. |
| 6,343,482 B1 | 2/2002 | Endo et al. |
| 6,352,538 B2 | 3/2002 | McGuire et al. |
| 6,358,253 B1 | 3/2002 | Torrie et al. |
| 6,419,678 B1 | 7/2002 | Asfora |
| 6,419,684 B1 | 7/2002 | Heisler et al. |
| 6,436,100 B1 | 8/2002 | Berger |
| 6,436,124 B1 | 8/2002 | Anderson et al. |
| 6,440,138 B1 | 8/2002 | Reiley et al. |
| 6,440,141 B1 | 8/2002 | Philippon |
| 6,447,518 B1 | 9/2002 | Krause et al. |
| 6,464,713 B2 | 10/2002 | Bonutti |
| 6,475,230 B1 | 11/2002 | Bonutti et al. |
| 6,478,800 B1 | 11/2002 | Fraser et al. |
| 6,485,504 B1 | 11/2002 | Johnson et al. |
| 6,500,195 B2 | 12/2002 | Bonutti |
| RE37,963 E | 1/2003 | Thal |
| 6,508,830 B2 | 1/2003 | Steiner |
| 6,511,498 B1 | 1/2003 | Fumex |
| 6,517,578 B2 | 2/2003 | Hein |
| 6,544,281 B2 | 4/2003 | ElAttrache et al. |
| 6,558,386 B1 | 5/2003 | Cragg |
| 6,558,390 B2 | 5/2003 | Cragg |
| 6,569,187 B1 | 5/2003 | Bonutti et al. |
| 6,572,635 B1 | 6/2003 | Bonutti |
| 6,575,979 B1 | 6/2003 | Cragg |
| 6,610,080 B2 | 8/2003 | Morgan |
| 6,635,073 B2 | 10/2003 | Bonutti |
| 6,638,279 B2 | 10/2003 | Bonutti |
| 6,638,283 B2 | 10/2003 | Thal |
| 6,641,597 B2 | 11/2003 | Burkhart et al. |
| 6,660,023 B2 | 12/2003 | McDevitt et al. |
| 6,712,822 B2 | 3/2004 | Re et al. |
| 6,716,234 B2 | 4/2004 | Grafton et al. |
| 6,740,090 B1 | 5/2004 | Cragg et al. |
| 6,780,188 B2 | 8/2004 | Clark et al. |
| 6,790,210 B1 | 9/2004 | Cragg et al. |
| 6,805,697 B1 | 10/2004 | Helm et al. |
| 6,824,552 B2 | 11/2004 | Robison et al. |
| 6,830,570 B1 | 12/2004 | Frey et al. |
| 6,863,672 B2 | 3/2005 | Reiley et al. |
| 6,878,150 B1 | 4/2005 | McGuire et al. |
| 6,887,259 B2 | 5/2005 | Lizardi |
| 6,893,445 B1 | 5/2005 | Revie et al. |
| 6,899,716 B2 | 5/2005 | Cragg |
| 6,921,403 B2 | 7/2005 | Cragg et al. |
| 6,923,811 B1 | 8/2005 | Carl et al. |
| 6,923,814 B1 | 8/2005 | Hildebrand et al. |
| 6,936,052 B2 | 8/2005 | Gellman et al. |
| 6,955,683 B2 | 10/2005 | Bonutti |
| 6,960,214 B2 | 11/2005 | Burkinshaw |
| 6,991,636 B2 | 1/2006 | Rose |
| 6,994,719 B2 | 2/2006 | Grafton |
| 6,994,725 B1 | 2/2006 | Goble |
| 6,995,683 B2 | 2/2006 | Smithson et al. |
| 7,008,431 B2 | 3/2006 | Simonson |
| 7,025,770 B2 | 4/2006 | McGuire et al. |
| 7,029,490 B2 | 4/2006 | Grafton et al. |
| 7,048,754 B2 | 5/2006 | Martin et al. |
| 7,060,073 B2 | 6/2006 | Frey et al. |
| 7,067,132 B2 | 6/2006 | Grabstein et al. |
| 7,077,863 B2 | 7/2006 | Schmieding et al. |
| 7,087,058 B2 | 8/2006 | Cragg |
| 7,087,073 B2 | 8/2006 | Bonutti |
| 7,204,839 B2 | 4/2007 | Dreyfuss et al. |
| 7,217,279 B2 | 5/2007 | Reese |
| 7,217,290 B2 | 5/2007 | Bonutti |
| 7,235,091 B2 | 6/2007 | Thornes |
| 7,241,297 B2 | 7/2007 | Shaolian et al. |
| 7,258,692 B2 | 8/2007 | Thelen et al. |
| 7,261,016 B2 | 8/2007 | Miller |
| 7,309,338 B2 | 12/2007 | Cragg |
| 7,326,215 B2 | 2/2008 | Myers et al. |
| 7,331,263 B2 | 2/2008 | Erickson et al. |
| 7,488,322 B2 | 2/2009 | Brunnett et al. |
| 7,488,329 B2 | 2/2009 | Thelen et al. |
| 7,494,490 B2 | 2/2009 | Justin |
| 7,500,977 B2 | 3/2009 | Assell et al. |
| 7,503,920 B2 | 3/2009 | Siegal |
| 7,520,898 B2 | 4/2009 | Re et al. |
| 7,563,266 B2 | 7/2009 | Camino et al. |
| 7,578,836 B2 | 8/2009 | Justin et al. |
| 7,585,300 B2 | 9/2009 | Cha |
| 7,601,155 B2 | 10/2009 | Petersen |
| 7,601,165 B2 | 10/2009 | Stone |
| 7,604,636 B1 | 10/2009 | Walters et al. |
| 7,608,098 B1 | 10/2009 | Stone et al. |
| 7,611,521 B2 | 11/2009 | Lubbers et al. |
| 7,621,912 B2 | 11/2009 | Harms et al. |
| 7,621,940 B2 | 11/2009 | Harms et al. |
| 7,651,509 B2 | 1/2010 | Bojarski et al. |
| 7,651,515 B2 | 1/2010 | Mack et al. |
| 7,658,751 B2 | 2/2010 | Stone et al. |
| 7,666,189 B2 | 2/2010 | Gerber et al. |
| 7,678,134 B2 | 3/2010 | Schmieding et al. |
| 7,749,250 B2 | 7/2010 | Stone et al. |
| 7,776,049 B1 | 8/2010 | Curran et al. |
| 7,803,173 B2 | 9/2010 | Burkhart et al. |
| 7,857,830 B2 | 12/2010 | Stone et al. |
| 7,875,057 B2 | 1/2011 | Cook et al. |
| 7,875,058 B2 | 1/2011 | Holmes, Jr. |
| 7,879,037 B2 | 2/2011 | Brunnett et al. |
| 7,892,256 B2 | 2/2011 | Grafton et al. |
| 7,901,431 B2 | 3/2011 | Shurnas |
| 7,905,903 B2 | 3/2011 | Stone et al. |
| 7,905,904 B2 | 3/2011 | Stone et al. |
| 7,909,851 B2 | 3/2011 | Stone et al. |
| 7,914,539 B2 | 3/2011 | Stone et al. |
| 7,918,874 B2 | 4/2011 | Siegal |
| 7,959,650 B2 | 6/2011 | Kaiser et al. |
| 7,981,117 B2 | 7/2011 | Newton et al. |
| 7,981,140 B2 | 7/2011 | Burkhart |
| 7,993,369 B2 | 8/2011 | Dreyfuss |
| 8,002,733 B2 | 8/2011 | Kraft et al. |
| 8,043,253 B2 | 10/2011 | Kraft et al. |
| 8,057,500 B2 | 11/2011 | Mitusina |
| 8,088,130 B2 | 1/2012 | Kaiser et al. |
| 8,114,088 B2 | 2/2012 | Miller |
| 8,118,836 B2 | 2/2012 | Denham et al. |
| 8,123,750 B2 | 2/2012 | Norton et al. |

(56) References Cited

U.S. PATENT DOCUMENTS

| | | |
|---|---|---|
| 8,128,640 B2 | 3/2012 | Harris et al. |
| 8,128,658 B2 | 3/2012 | Kaiser et al. |
| 8,128,669 B2 | 3/2012 | Bonutti |
| 8,133,231 B2 | 3/2012 | Martinek et al. |
| 8,137,382 B2 | 3/2012 | Denham et al. |
| 8,147,514 B2 | 4/2012 | Bonutti |
| 8,162,997 B2 | 4/2012 | Struhl |
| 8,172,846 B2 | 5/2012 | Brunnett et al. |
| 8,231,654 B2 | 7/2012 | Kaiser et al. |
| 8,231,674 B2 | 7/2012 | Albertorio et al. |
| 8,241,305 B2 | 8/2012 | Stone |
| 8,267,959 B2 | 9/2012 | Fallman |
| 8,273,106 B2 | 9/2012 | Stone et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,317,825 B2 | 11/2012 | Stone |
| 8,337,525 B2 | 12/2012 | Stone et al. |
| 8,361,113 B2 | 1/2013 | Stone et al. |
| 8,398,678 B2 | 3/2013 | Baker et al. |
| 8,439,976 B2 | 5/2013 | Albertorio et al. |
| 8,591,578 B2 | 11/2013 | Albertorio et al. |
| 8,623,051 B2 | 1/2014 | Bojarski et al. |
| 8,663,324 B2 | 3/2014 | Schmieding et al. |
| 8,801,800 B2 | 8/2014 | Bagga et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 8,936,620 B2 | 1/2015 | Kaiser et al. |
| 2002/0019635 A1 | 2/2002 | Wenstrom et al. |
| 2002/0188301 A1 | 12/2002 | Dallara et al. |
| 2003/0032961 A1 | 2/2003 | Pelo et al. |
| 2003/0176919 A1 | 9/2003 | Schmieding |
| 2003/0195565 A1 | 10/2003 | Bonutti |
| 2003/0220646 A1 | 11/2003 | Thelen et al. |
| 2003/0233098 A1 | 12/2003 | Markworth |
| 2004/0010264 A1 | 1/2004 | Acker et al. |
| 2004/0010287 A1 | 1/2004 | Bonutti |
| 2004/0030346 A1 | 2/2004 | Frey et al. |
| 2004/0049194 A1 | 3/2004 | Harvie et al. |
| 2004/0073227 A1 | 4/2004 | Dreyfuss et al. |
| 2004/0073306 A1 | 4/2004 | Eichhorn et al. |
| 2004/0092933 A1 | 5/2004 | Shaolian et al. |
| 2004/0193217 A1 | 9/2004 | Lubbers et al. |
| 2004/0260300 A1 | 12/2004 | Gorensek et al. |
| 2004/0267277 A1 | 12/2004 | Zannis et al. |
| 2004/0267317 A1 | 12/2004 | Higgins et al. |
| 2005/0015153 A1 | 1/2005 | Goble et al. |
| 2005/0033362 A1 | 2/2005 | Grafton |
| 2005/0070906 A1 | 3/2005 | Clark et al. |
| 2005/0137600 A1 | 6/2005 | Jacobs et al. |
| 2005/0137601 A1 | 6/2005 | Assell et al. |
| 2005/0143741 A1 | 6/2005 | Timmermans et al. |
| 2005/0177168 A1 | 8/2005 | Brunnett et al. |
| 2005/0187537 A1 | 8/2005 | Loeb et al. |
| 2005/0203527 A1 | 9/2005 | Carrison et al. |
| 2005/0228399 A1 | 10/2005 | Kubo et al. |
| 2005/0251159 A1 | 11/2005 | Ewers et al. |
| 2005/0251208 A1 | 11/2005 | Elmer et al. |
| 2006/0001518 A1 | 1/2006 | Hayashi et al. |
| 2006/0004369 A1 | 1/2006 | Patel et al. |
| 2006/0015108 A1 | 1/2006 | Bonutti |
| 2006/0074434 A1 | 4/2006 | Wenstrom et al. |
| 2006/0100631 A1 | 5/2006 | Sullivan et al. |
| 2006/0155329 A1 | 7/2006 | Grafton et al. |
| 2006/0178748 A1 | 8/2006 | Dinger et al. |
| 2006/0189993 A1 | 8/2006 | Stone |
| 2006/0190042 A1 | 8/2006 | Stone et al. |
| 2006/0212055 A1 | 9/2006 | Karabey et al. |
| 2006/0247641 A1 | 11/2006 | Re et al. |
| 2006/0247642 A1 | 11/2006 | Stone et al. |
| 2006/0282085 A1 | 12/2006 | Stone et al. |
| 2006/0293689 A1 | 12/2006 | Miller et al. |
| 2007/0010843 A1 | 1/2007 | Green |
| 2007/0010857 A1 | 1/2007 | Sugimoto et al. |
| 2007/0032800 A1 | 2/2007 | Ortiz et al. |
| 2007/0093840 A1 | 4/2007 | Pacelli et al. |
| 2007/0191853 A1 | 8/2007 | Stone |
| 2007/0213734 A1 | 9/2007 | Bleich et al. |
| 2007/0213735 A1 | 9/2007 | Saadat et al. |
| 2007/0225721 A1 | 9/2007 | Thelen et al. |
| 2007/0233151 A1 | 10/2007 | Chudik |
| 2007/0260259 A1 | 11/2007 | Fanton et al. |
| 2007/0288031 A1 | 12/2007 | Dreyfuss et al. |
| 2008/0027446 A1 | 1/2008 | Stone et al. |
| 2008/0027457 A1 | 1/2008 | Dienst et al. |
| 2008/0046009 A1 | 2/2008 | Albertorio et al. |
| 2008/0058816 A1 | 3/2008 | Philippon et al. |
| 2008/0065080 A1 | 3/2008 | Assell et al. |
| 2008/0065092 A1 | 3/2008 | Assell et al. |
| 2008/0071282 A1 | 3/2008 | Assell et al. |
| 2008/0109037 A1 | 5/2008 | Steiner et al. |
| 2008/0114399 A1 | 5/2008 | Bonutti |
| 2008/0132932 A1 | 6/2008 | Hoeppner et al. |
| 2008/0140078 A1 | 6/2008 | Nelson et al. |
| 2008/0140116 A1 | 6/2008 | Bonutti |
| 2008/0147063 A1 | 6/2008 | Cauldwell et al. |
| 2008/0154275 A1 | 6/2008 | Assell et al. |
| 2008/0161814 A1 | 7/2008 | McAllister et al. |
| 2008/0167660 A1 | 7/2008 | Moreau et al. |
| 2008/0188854 A1 | 8/2008 | Moser |
| 2008/0188935 A1 | 8/2008 | Saylor et al. |
| 2008/0249481 A1 | 10/2008 | Crainich et al. |
| 2008/0255613 A1 | 10/2008 | Kaiser et al. |
| 2008/0275431 A1 | 11/2008 | Stone et al. |
| 2008/0306483 A1 | 12/2008 | Iannarone |
| 2008/0312689 A1 | 12/2008 | Denham et al. |
| 2009/0012526 A1 | 1/2009 | Fletcher |
| 2009/0018654 A1 | 1/2009 | Schmieding et al. |
| 2009/0024130 A1 | 1/2009 | Lombardo |
| 2009/0054928 A1 | 2/2009 | Denham et al. |
| 2009/0062854 A1 | 3/2009 | Kaiser et al. |
| 2009/0076514 A1 | 3/2009 | Haines |
| 2009/0082805 A1 | 3/2009 | Kaiser et al. |
| 2009/0099554 A1 | 4/2009 | Forster et al. |
| 2009/0105775 A1 | 4/2009 | Mitchell et al. |
| 2009/0112270 A1 | 4/2009 | Lunn et al. |
| 2009/0131940 A1 | 5/2009 | Brunnett et al. |
| 2009/0138015 A1 | 5/2009 | Conner et al. |
| 2009/0138042 A1 | 5/2009 | Thal |
| 2009/0143784 A1 | 6/2009 | Petersen et al. |
| 2009/0149858 A1 | 6/2009 | Fanelli et al. |
| 2009/0157081 A1 | 6/2009 | Homan et al. |
| 2009/0157124 A1 | 6/2009 | Ferragamo et al. |
| 2009/0160112 A1 | 6/2009 | Ostrovsky |
| 2009/0171359 A1 | 7/2009 | Sterrett |
| 2009/0192468 A1 | 7/2009 | Stone |
| 2009/0194446 A1 | 8/2009 | Miller et al. |
| 2009/0198258 A1 | 8/2009 | Workman |
| 2009/0216238 A1 | 8/2009 | Stark |
| 2009/0216243 A1 | 8/2009 | Re |
| 2009/0234451 A1 | 9/2009 | Manderson |
| 2009/0248029 A1 | 10/2009 | Paulos |
| 2009/0265002 A1 | 10/2009 | Re et al. |
| 2009/0306671 A1 | 12/2009 | McCormack et al. |
| 2009/0306711 A1* | 12/2009 | Stone et al. ............... 606/232 |
| 2009/0312763 A1 | 12/2009 | McCormack et al. |
| 2009/0312776 A1 | 12/2009 | Kaiser et al. |
| 2009/0312792 A1 | 12/2009 | Fallin et al. |
| 2009/0318961 A1 | 12/2009 | Stone et al. |
| 2009/0326538 A1 | 12/2009 | Sennett et al. |
| 2010/0049196 A1 | 2/2010 | Re |
| 2010/0057045 A1 | 3/2010 | Albritton, IV et al. |
| 2010/0076440 A1 | 3/2010 | Pamichev et al. |
| 2010/0082033 A1 | 4/2010 | Germain |
| 2010/0087857 A1 | 4/2010 | Stone et al. |
| 2010/0121332 A1 | 5/2010 | Crainich et al. |
| 2010/0121333 A1 | 5/2010 | Crainich et al. |
| 2010/0145384 A1 | 6/2010 | Stone et al. |
| 2010/0152739 A1 | 6/2010 | Sidebotham et al. |
| 2010/0160962 A1 | 6/2010 | Dreyfuss et al. |
| 2010/0185238 A1 | 7/2010 | Cauldwell et al. |
| 2010/0185283 A1 | 7/2010 | Baird et al. |

(56) References Cited

U.S. PATENT DOCUMENTS

| | | |
|---|---|---|
| 2010/0191241 A1 | 7/2010 | McCormack et al. |
| 2010/0211075 A1 | 8/2010 | Stone |
| 2010/0241121 A1 | 9/2010 | Logan et al. |
| 2010/0249786 A1 | 9/2010 | Schmieding et al. |
| 2010/0268275 A1 | 10/2010 | Stone et al. |
| 2010/0292732 A1 | 11/2010 | Hirotsuka et al. |
| 2010/0292792 A1 | 11/2010 | Stone et al. |
| 2010/0305709 A1 | 12/2010 | Metzger et al. |
| 2011/0015674 A1 | 1/2011 | Howard et al. |
| 2011/0015675 A1 | 1/2011 | Howard et al. |
| 2011/0022083 A1 | 1/2011 | DiMatteo et al. |
| 2011/0022084 A1 | 1/2011 | Sengun et al. |
| 2011/0046625 A1 | 2/2011 | Boileau et al. |
| 2011/0054526 A1 | 3/2011 | Stone et al. |
| 2011/0087247 A1 | 4/2011 | Fung et al. |
| 2011/0087280 A1 | 4/2011 | Albertorio |
| 2011/0087284 A1 | 4/2011 | Stone et al. |
| 2011/0098727 A1* | 4/2011 | Kaiser et al. .................. 606/144 |
| 2011/0106089 A1 | 5/2011 | Brunnett et al. |
| 2011/0106153 A1 | 5/2011 | Stone et al. |
| 2011/0125189 A1 | 5/2011 | Stoll, Jr. et al. |
| 2011/0152927 A1 | 6/2011 | Deng et al. |
| 2011/0160767 A1 | 6/2011 | Stone et al. |
| 2011/0160768 A1 | 6/2011 | Stone et al. |
| 2011/0184516 A1 | 7/2011 | Baird et al. |
| 2011/0208194 A1 | 8/2011 | Steiner et al. |
| 2011/0208239 A1 | 8/2011 | Stone et al. |
| 2011/0208240 A1 | 8/2011 | Stone et al. |
| 2011/0218538 A1 | 9/2011 | Sherman et al. |
| 2011/0218625 A1 | 9/2011 | Berelsman et al. |
| 2011/0224799 A1 | 9/2011 | Stone |
| 2011/0264141 A1 | 10/2011 | Denham et al. |
| 2011/0270278 A1 | 11/2011 | Overes et al. |
| 2011/0270293 A1 | 11/2011 | Malla et al. |
| 2011/0270306 A1 | 11/2011 | Denham et al. |
| 2011/0295279 A1 | 12/2011 | Stone et al. |
| 2011/0301708 A1 | 12/2011 | Stone et al. |
| 2011/0319896 A1 | 12/2011 | Papenfuss et al. |
| 2012/0004672 A1 | 1/2012 | Giap et al. |
| 2012/0041485 A1 | 2/2012 | Kaiser et al. |
| 2012/0041486 A1 | 2/2012 | Stone et al. |
| 2012/0046693 A1* | 2/2012 | Denham et al. ................ 606/232 |
| 2012/0053629 A1* | 3/2012 | Reiser et al. .................. 606/232 |
| 2012/0053630 A1 | 3/2012 | Denham et al. |
| 2012/0053641 A1 | 3/2012 | Meridew |
| 2012/0059417 A1 | 3/2012 | Norton et al. |
| 2012/0059418 A1 | 3/2012 | Denham et al. |
| 2012/0071976 A1 | 3/2012 | May et al. |
| 2012/0089193 A1 | 4/2012 | Stone et al. |
| 2012/0095470 A1* | 4/2012 | Kaiser et al. .................. 606/80 |
| 2012/0095556 A1 | 4/2012 | Re et al. |
| 2012/0109142 A1 | 5/2012 | Dayan |
| 2012/0109156 A1 | 5/2012 | Overes et al. |
| 2012/0109194 A1 | 5/2012 | Miller et al. |
| 2012/0116452 A1 | 5/2012 | Stone et al. |
| 2012/0123474 A1 | 5/2012 | Zajac et al. |
| 2012/0150203 A1 | 6/2012 | Brady et al. |
| 2012/0150297 A1 | 6/2012 | Denham et al. |
| 2012/0150301 A1 | 6/2012 | Gamache et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0172986 A1 | 7/2012 | Stone et al. |
| 2012/0179254 A1 | 7/2012 | Saliman |
| 2012/0180291 A1 | 7/2012 | Oren et al. |
| 2012/0197271 A1 | 8/2012 | Astorino et al. |
| 2012/0203288 A1 | 8/2012 | Lange et al. |
| 2012/0209325 A1 | 8/2012 | Gagliano et al. |
| 2012/0245585 A1 | 9/2012 | Kaiser et al. |
| 2012/0253355 A1 | 10/2012 | Murray et al. |
| 2012/0290002 A1 | 11/2012 | Astorino |
| 2012/0290004 A1 | 11/2012 | Lombardo et al. |
| 2012/0290006 A1 | 11/2012 | Collins et al. |
| 2012/0296345 A1 | 11/2012 | Wack et al. |
| 2012/0296427 A1 | 11/2012 | Conner et al. |
| 2012/0303046 A1 | 11/2012 | Stone et al. |
| 2013/0012962 A1 | 1/2013 | Stone |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0053897 A1 | 2/2013 | Brown et al. |
| 2013/0072989 A1 | 3/2013 | Overes et al. |
| 2013/0085568 A1 | 4/2013 | Smith et al. |
| 2013/0096611 A1 | 4/2013 | Sullivan |
| 2013/0096612 A1 | 4/2013 | Zajac et al. |
| 2013/0110165 A1 | 5/2013 | Burkhart et al. |
| 2013/0131722 A1 | 5/2013 | Marchand et al. |
| 2013/0165972 A1 | 6/2013 | Sullivan |
| 2013/0190819 A1 | 7/2013 | Norton |
| 2013/0237997 A1 | 9/2013 | Arai et al. |
| 2013/0245700 A1 | 9/2013 | Choinski |
| 2013/0268000 A1 | 10/2013 | Harner et al. |
| 2013/0296931 A1 | 11/2013 | Sengun |
| 2013/0317544 A1 | 11/2013 | Ferguson et al. |
| 2013/0325063 A1 | 12/2013 | Norton et al. |
| 2013/0345749 A1 | 12/2013 | Sullivan et al. |
| 2014/0039503 A1 | 2/2014 | Pilgeram |
| 2014/0163679 A1 | 6/2014 | Re et al. |
| 2014/0188163 A1 | 7/2014 | Sengun |

FOREIGN PATENT DOCUMENTS

| | | |
|---|---|---|
| DE | 4243715 A1 | 7/1994 |
| DE | 19503504 A1 | 3/1996 |
| EP | 153831 A2 | 9/1985 |
| EP | 253526 A1 | 1/1988 |
| EP | 0440371 A1 | 8/1991 |
| EP | 0611551 A1 | 8/1994 |
| EP | 1155776 A2 | 11/2001 |
| EP | 1369089 A2 | 12/2003 |
| EP | 2544607 A1 | 1/2013 |
| EP | 2596755 A2 | 5/2013 |
| EP | 2662030 A1 | 11/2013 |
| EP | 2662032 A1 | 11/2013 |
| FR | 1166884 A | 11/1958 |
| FR | 2606996 A1 | 5/1988 |
| FR | 2676638 A1 | 11/1992 |
| GB | 2093353 A | 9/1982 |
| WO | 9511631 A1 | 5/1995 |
| WO | 9722301 A1 | 6/1997 |
| WO | 00/44291 A1 | 8/2000 |
| WO | 0128457 A1 | 4/2001 |
| WO | 03007861 A1 | 1/2003 |
| WO | 2007/010389 A1 | 1/2007 |
| WO | 2008128075 A1 | 10/2008 |
| WO | 2009105880 A1 | 9/2009 |
| WO | 2011112371 A1 | 9/2011 |
| WO | 2012134999 A1 | 10/2012 |
| WO | 2012158583 A1 | 11/2012 |

OTHER PUBLICATIONS

Burkinshaw, U.S. Appl. No. 60/418,545, filed Oct. 15, 2002.
Chen et al., Journal of Orthopaedic Research, pp. 1432-1438, Nov. 2009.
Chen et al., Poster No. 538, 54th Annual Meeting of the Orthopaedic Research Society, San Francisco, CA Mar. 2008.
Cole et al., American Journal of Sports Medicine, vol. XX, No. X, 2011.
Conmed: Linvatec: Shoulder Restoration System Y-Knot 1.3mnn All Suture Anchor, © 2011 Linvatec Corporation, a subsidiary of ConMed Corporation—CBR 3057 (4 pages).
European Search Report, EP 10173568, dated Nov. 30, 2010.
HHS Tube, Fort Wayne Metals Research Products Corp., 2009.
International Search Report PCT/US2010/042264, dated Sep. 30, 2010.
Medtronic, The VISAO High-Speed Otologic Drill Catalog, 2007.
Perthes, German Surgery Periodical, vol. 85, Commermorative Publication, pp. 2-18, 1906.

(56) References Cited

OTHER PUBLICATIONS

Perthes, Ober Operationen bel habitueller Schulterluxaton, X, pp. 199-227, 85.
Sugaya et al., Journal of Bone and Joint Surgery, vol. 85-A, No. 5, pp. 878-884, May 2003.
U.S. Appl. No. 13/368,730, filed Feb. 8, 2012.
U.S. Appl. No. 13/588,592, filed Aug. 17, 2012.
U.S. Appl. No. 13/783,804, filed Mar. 4, 2013.
U.S. Appl. No. 61/679,336, filed Aug. 3, 2012.
U.S. Appl. No. 13/085,882, filed Apr. 13, 2011.
U.S. Appl. No. 13/588,586, filed Aug. 17, 2012.
U.S. Appl. No. 13/303,849, filed Nov. 23, 2011.
Extended European Search Report for Application No. EP 12164104 dated Jul. 11, 2012.
Extended European Search Report for Application No. EP14159656 dated Jun. 6, 2014.
International Search Report and Written Opinion for Application No. PCT/US2014/021231 dated Jun. 25, 2014.
U.S. Appl. No. 13/792,982, filed Mar. 11, 2013.
Extended European Search Report for Application No. EP14157129 dated Oct. 9, 2014.
Partial International Search Report for Application No. PCT/US2014/069087 dated Mar. 12, 2015.
International Search Report and Written Opinion for Application No. PCT/US2014/069087 dated Jun. 17, 2015.

* cited by examiner

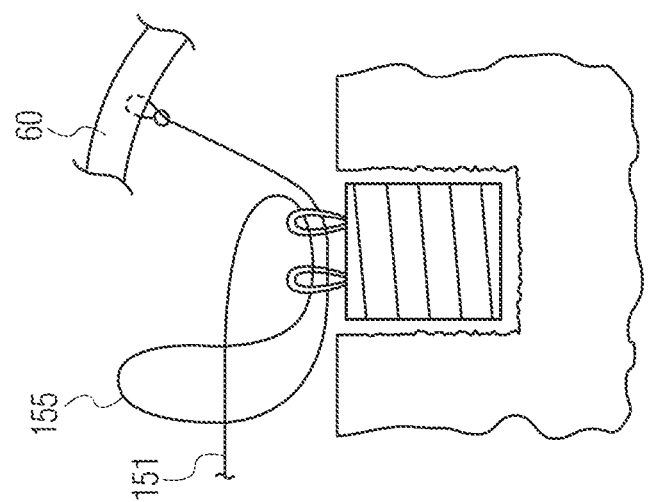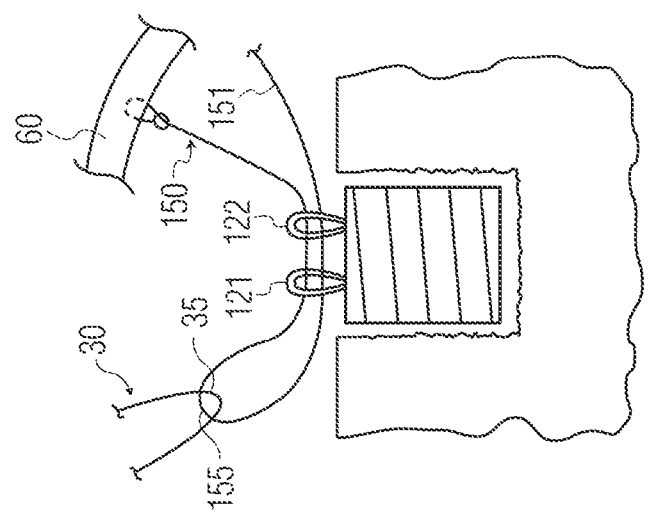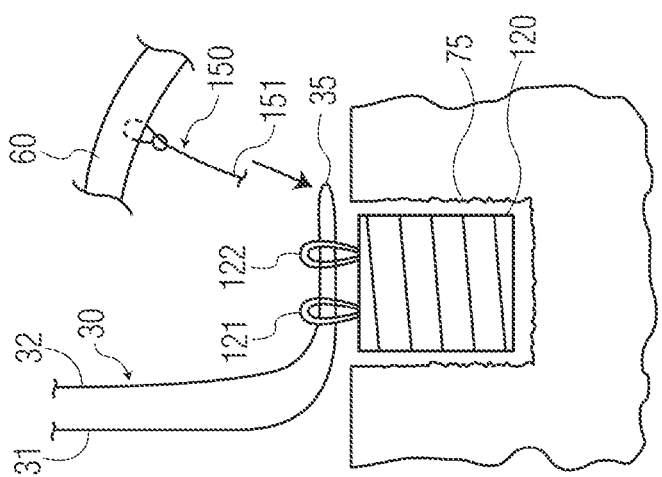

KNOTLESS FILAMENTARY FIXATION DEVICES, ASSEMBLIES AND SYSTEMS AND METHODS OF ASSEMBLY AND USE

BACKGROUND OF THE INVENTION

A recent trend in tissue anchor and suture anchor devices is the "soft" device, also referred to as a "filamentary" fixation device, in which the device itself is constructed of a filamentary material, such as suture or the like. Such filamentary fixation devices can replace traditional metal or hard polymer devices in numerous soft tissue repair and replacement surgical procedures. Such filamentary fixation devices may provide solutions to various problems encountered with traditional metal or hard polymer devices. In many instances, such traditional devices tend to be large in diameter, and must include sufficient material, or other additional structures, to withstand the forces pulling against the device, whether via a suture or directly against the device itself. The size of such devices may limit the possible implantation locations in the body, as sufficient bone mass is required to accommodate the device. Moreover, a large hole must be drilled into the bone to allow for passage of the device through the cortical layer and into the cancellous bone. The larger drill holes may be too invasive resulting in excessive loss of healthy bone, or creation of a large repair site.

Despite the many benefits these filamentary fixation devices provide, such devices to date cannot be used to perform knotless surgical procedures, that is, surgical procedures using filaments (such as sutures or the like) where the filament is secured without the need of tying knots, such as half hitches or the like. Such surgical procedures are beneficial as knots have the tendency to loosen over time, thereby reducing the likelihood of a successful repair. Additionally, knot tying can take up an inordinate amount of time during a surgical procedure, as well as making the suture more susceptible to breakage, particularly at the location of the knot itself, which is commonly known as a weak point of surgical repairs. Furthermore, the stack of knots that is created after tying the sufficient amount of half hitches or the like can be undesirable as they interface with surrounding anatomy such as tissue, bone, and cartilage. Therefore, there is a need for improved filamentary fixation devices capable for use in knotless surgical procedures.

BRIEF SUMMARY OF THE INVENTION

Generally, the present invention includes various devices, assemblies, systems and methods of assembly and use including fixation devices, assemblies and systems, and specifically filamentary fixation devices, assemblies and systems, suitable for knotless applications. In one embodiment, the present invention includes a filamentary sleeve, a filamentary shuttle and a length of filament. Together, the sleeve, shuttle and length of filament can be assembled and used to secure tissue without the use of knots such as half hitches and the like. Such filamentary fixation devices may be used in a variety of surgical procedures to repair tissue, and in particular various soft tissues. While the majority of embodiments disclosed herein relate to the use of the filamentary devices, assemblies and systems of the present invention as a "suture anchor" for placement in bone, and to attach, reattach or otherwise secure soft tissue thereto, other uses of the filamentary devices, assemblies and systems are also possible, examples of which are also described herein.

In another embodiment, the present invention includes a fixation assembly for securing tissue including a fixation device, a filamentary shuttle positioned through at least one portion of the device, the filamentary shuttle including an outer filament having a first end and a second end, and a length therebetween, and an inner filament having a first end and a second end, and a length therebetween, wherein the second end of the inner filament includes a loop structure, and a length of filament having a first free end, a second free end and a length therebetween, the length of filament adapted to have a working relationship with the tissue. The fixation device may be a filamentary sleeve formed of filament, and the filamentary sleeve can be adapted to be implanted in a tissue and deploy therein to become fixedly secured to the tissue. In a specific example, the filamentary sleeve can be adapted to be positioned within a bore hole in a bone such that, once deployed, the filamentary sleeve is fixedly secured within the bore hole.

Further as to this assembly, wherein each of the filamentary sleeve, filamentary shuttle outer filament, filamentary shuttle inner filament and length of filament are formed of suture, wherein the filamentary sleeve is formed of a suture having a larger inner diameter than the filamentary shuttle outer filament, and the filamentary shuttle outer filament is formed of a suture having a larger diameter than both the inner filament and the length of filament.

In a further embodiment, the present invention includes a filamentary fixation system for securing tissue including a filamentary sleeve formed of filament; a filamentary shuttle positioned through at least one portion of the filamentary sleeve, the filamentary shuttle having an eyelet; a length of filament having a first free end, a second free end and a length therebetween, the length of filament adapted to have a working relationship with the tissue; and an instrument adapted to implant the filamentary sleeve into an anatomical location adjacent the tissue to be secured. Further, the filamentary shuttle further can include a first end, a second end, a length between the first and second ends, an interior passageway along at least a portion of the length and an inner filament positioned within the interior passageway of the filamentary shuttle, wherein a portion of the inner filament can extend out of the interior passageway and the portion includes the eyelet. Additionally, the instrument may be adapted to position the filamentary sleeve within a bore hole in a bone and the filamentary sleeve is adapted to deploy within the bore hole such that, once deployed, the filamentary sleeve is fixedly secured within the bore hole.

In yet another embodiment, the present invention includes a method of securing tissue using a filamentary construct, the method having the steps of passing a length of filament through or around tissue; implanting a filamentary sleeve, formed of filament, into tissue; and passing at least a portion of the length of filament at least partially through the filamentary sleeve to form a one-way cleat. The filamentary sleeve can be implanted into tissue, such as bone. The method can include the additional step of, upon implanting the sleeve in bone, deploying the sleeve to fixedly secure the sleeve relative to the bone.

Further to this embodiment, the filamentary sleeve can include a filamentary shuttle and the step of passing the portion of the length of filament may include engaging the portion of the length of filament with the filamentary shuttle and pulling the portion of the length of filament through the filamentary sleeve. Additionally, in one example, the one-way cleat can be formed by continuing to pull at least a portion of the length of filament into and through the sleeve, thereby forming a loop configuration on the length of filament, wherein in this position, the length of filament is folded over itself, forming the loop configuration at one end and at least one filament free end at the other end; passing the at least one free end of the length of filament through the loop configuration; and tensioning the at least one free end such that the loop configuration travels towards and into the filamentary sleeve, the length of filament adapted to apply tension to the tissue, and the at least one filament free end, passed through the loop configuration, is secured within the loop configuration.

In still another embodiment, the present invention includes a method of securing tissue using a filamentary construct, the method having the steps of obtaining a filamentary sleeve having a length along a longitudinal axis and a pathway therethrough and a filamentary shuttle positioned at least partially through the pathway; engaging a length of filament with the filamentary shuttle, the length of filament in working relationship with the tissue; pulling at least a portion of the length of filament into the filamentary sleeve; continuing to pull at least a portion of the length of filament into and through the sleeve, thereby forming a loop configuration on the length of filament, wherein in this position, the length of filament is folded over itself, forming the loop configuration at one end and at least one filament free end at the other end; passing the at least one free end of the length of filament through the loop configuration; and tensioning the at least one free end such that the loop configuration travels towards and into the filamentary sleeve, the length of filament adapted to apply tension to the tissue, and the at least one filament free end, passed through the loop configuration, is secured within the loop configuration.

Continuing with this embodiment, the filamentary shuttle may include an eyelet formed by an inner filament, positioned within an interior passageway of the filamentary shuttle, wherein a portion of the inner filament extends out of the interior passageway and the portion includes the eyelet. The method can further include, prior to the step of engaging the length of filament with the filamentary shuttle, implanting the filamentary sleeve into a prepared bore hole in a bone and deploying the filamentary sleeve such that the filamentary sleeve is fixedly secured within the bore hole.

In another embodiment, the present invention includes a method of manufacture or assembly, wherein the method includes the steps of obtaining a filamentary sleeve having a length along a longitudinal axis and a pathway therethrough and a filamentary shuttle positioned at least partially through the pathway; engaging a length of filament with the filamentary shuttle; pulling at least a portion of the length of filament into the filamentary sleeve; continuing to pull at least a portion of the length of filament into and through the sleeve, thereby forming a loop configuration on the length of filament, wherein in this position, the length of filament is folded over itself, forming the loop configuration at one end and at least one filament free end at the other end; passing the at least one free end of the length of filament through the loop configuration; and tensioning the at least one free end such that the loop configuration travels towards and into the filamentary sleeve and the at least one filament free end, passed through the loop configuration, is secured within the loop configuration.

In yet a further embodiment, the present invention includes a fixation device for securing tissue including a filamentary fixation device and a length of filament, wherein the filament is positioned through at least a portion of the filamentary fixation device to secure a tissue to the filamentary fixation device, where the tissue is secured without tying any knots.

In this embodiment, both the fixation device and filament may be formed of suture, and the filament is passed through the at least a portion of the fixation device, and secured thereto, by forming a one-way cleat using only the fixation device and filament. Specifically, the one-way cleat can be formed by pulling at least a portion of the filament into and through the fixation device, thereby forming a loop configuration on the filament, wherein in this position, the filament is folded over itself, forming the loop configuration at one end and at least one filament free end at the other end; passing the at least one free end of the filament through the loop configuration; and tensioning the at least one free end such that the loop configuration travels towards and into the fixation device, the filament adapted to apply tension to the tissue, and the at least one filament free end, passed through the loop configuration, is secured within the loop configuration.

In another embodiment, the present invention includes a system for the repair of soft tissue including at least one filamentary fixation assembly, at least one instrument for insertion of the filamentary fixation assembly, and a surgical procedure. The surgical procedure may include instructions or protocol for using the filamentary fixation assembly and instrument to repair soft tissue.

In an associated embodiment, the present invention includes a method of providing instructions or information to practice any of the various methods of performing soft tissue repair described herein. For example, the method may include supplying a surgical protocol, or like document, to provide step-by-step instructions for performing any of the method embodiments of the present invention.

BRIEF DESCRIPTION OF THE DRAWINGS

FIG. 3A illustrates one embodiment of the use of the filamentary assembly of FIG. 1A in which the assembly is positioned in a bore hole in bone in a first configuration, while

FIGS. 11A-C illustrate yet another embodiment of a method of use or assembly.

DETAILED DESCRIPTION

The fixation devices, assemblies, systems, kits and associated methods of use, manufacture and assembly, of the present invention are intended for use in the repair, reattachment, replacement or otherwise securement of tissue, including both hard tissue (i.e., bone or the like) and soft tissue. Soft tissue may be, for example, meniscus, cartilage, capsule, ligaments and tendons, replacement grafts of any of these soft tissues, or the like. While many of the exemplary methods disclosed herein are directed towards the use of the filamentary fixation devices, assemblies and systems as a suture anchor for implantation into a bone hole, other uses, some of which are described herein, are also envisioned. As used herein, "proximal" or "proximally" means closer to or towards an operator, e.g., surgeon, while "distal" or "distally" means further from or away from the operator.

As used herein, the term "filament" or "filamentary" is defined as a suture or other thread-like material. Such filaments may be constructed of synthetic material (e.g., PLGA, UHMWPE (ultra high molecular weight polyethylene), polyester, PEEK, Nylon, polypropylene, aramids (for example, Kevlar®-based fibers) or the like, or blends thereof), organic material (silk, animal tendon, or the like or blends thereof), or blends of both one or more organic materials and one or more synthetic materials. Alternatively, filaments may include thin metal wires. While any of these materials may be used, it is preferable, and is disclosed herein, that the various filaments or filamentary aspects of the present invention be constructed out of suture, such as UHMWPE, polyester or blends thereof.

Figure 1A:
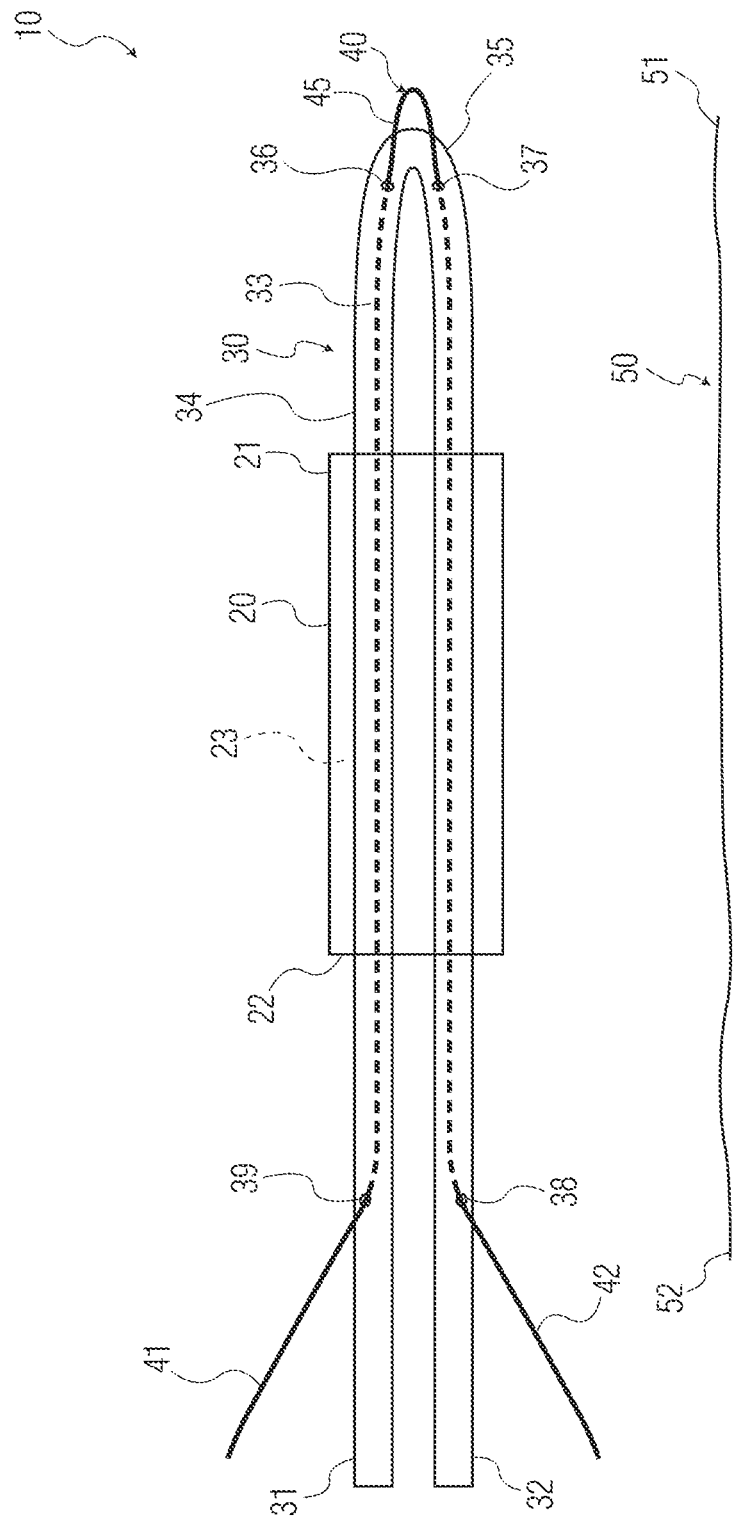
FIGS. 1A and 1B illustrate various embodiments of a filamentary assembly.

In one embodiment, illustrated in detail in FIG. 1A, a filamentary fixation device, assembly or system, designated as filamentary fixation assembly 10, of the present invention includes a filamentary sleeve 20, a filamentary shuttle 30 and a length of filament 50.

Figure 1B:
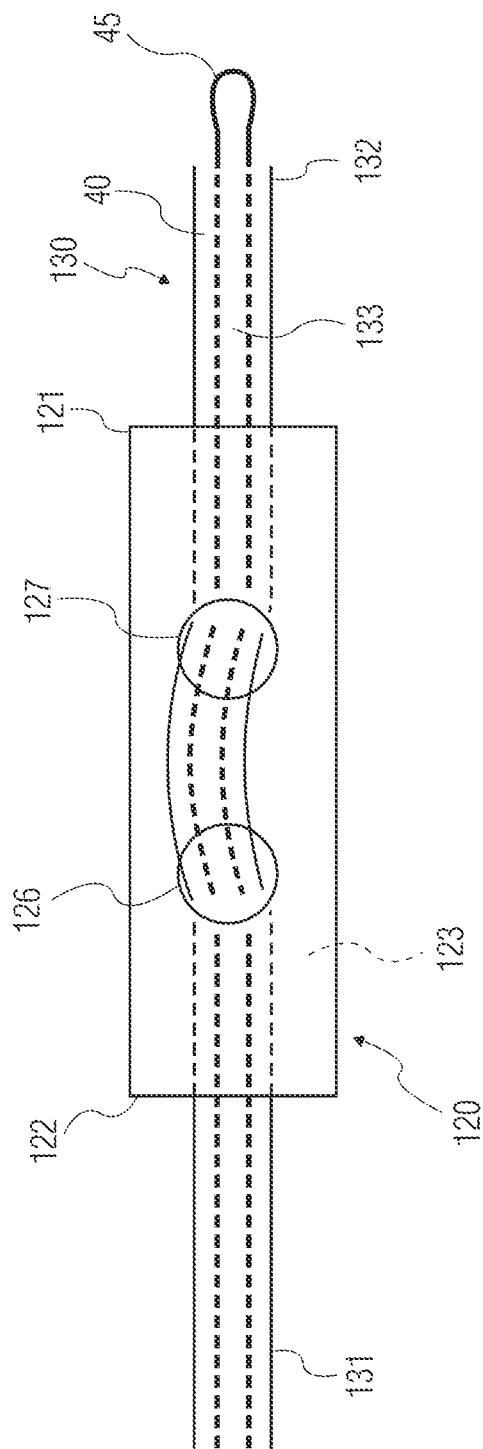

The filamentary sleeve 20 includes a generally cylindrical shape along a longitudinal axis, defined by a first end 21 and a second end 22, and a hollow pathway 23 extending therethrough along the longitudinal axis. While this filamentary sleeve 20 is one embodiment, it is envisioned that alternative configurations of the sleeve 20 may also be incorporated into the various assemblies, systems, and methods, and may include alternative shapes, sizes, or features as desired, one example of which is shown in FIG. 1B, discussed below. Additional examples of alternative configurations are disclosed in U.S. Provisional Application No. 61/679,336, filed Aug. 3, 2012, U.S. application Ser. No. 13/303,849, filed Nov. 23, 2011, Ser. No. 13/588,586, filed Aug. 17, 2012, and Ser. No. 13/588,592, filed Aug. 17, 2012, and U.S. Pat. Nos. 5,989,252 and 6,511,498, the entireties of which are incorporated by reference herein as if fully set forth herein and all of which are assigned to the same entity as the present application. Another exemplary filamentary sleeve for use in the present invention is the ICONIX™ line of filamentary fixation products (Howmedical Osteonics, Mahwah, N.J.). Other alternative configurations are also envisioned. For example the sleeve 20 may be constructed by braiding multiple filaments together, such that the sleeve is a braided or woven structure.

The filamentary shuttle 30 includes a first end or tail 31 and a second end or tail 32, a length therebetween, and an interior passageway 33 along at least a portion of the length. The shuttle 30 may also include at least two openings 36, 37, and optionally at least four openings 36, 37, 38, 39 (as in FIG. 1), which extend through a sidewall from the interior passageway 33 to an outer surface 34 of the shuttle. As the shuttle 30 is preferably constructed from a length of suture having a hollow core, the interior passageway 33 would extend along the entire length of the shuttle filament 30. However, if the shuttle is constructed of another material, or is formed from a unique braid, or the like, the passageway may not extend the entire length of the shuttle, though it should at least extend along the length of the shuttle spanning the distance between the at least two openings, or at least four openings, if four openings are present (as illustrated in FIG. 1), for reasons discussed further below. Shuttle 30 can also include a structure for engaging the length of filament 50 (described in detail below), such as a loop structure as exemplified by loop configuration 35.

Additionally, an inner filament 40 can be positioned within at least a portion of the interior passageway 33 of the filamentary shuttle 30. As illustrated in FIG. 1, for example, the inner filament 40 can extend through the passageway 33, from end 31 and towards the loop configuration 35, and out of opening 36. The inner filament 40 can continue outside of the passageway 33 and to opening 37, forming a structure for engaging the length of filament 50 (described in detail below) outside of the passageway 30 and at a position on or adjacent to the loop configuration 35. The inner filament 40 can then pass through opening 37 and back into passageway 30, towards end 32. This engaging structure can be a loop structure as is exemplified by filament eyelet 45. The inner filament 40 first and second ends 41, 42 may remain in position within the inner passageway 33, may extend to and through the first and second ends 31, 32 of the shuttle 30, or, as illustrated, exit the passageway 33 through additional openings 38, 39.

The filamentary shuttle 30, with or without the inner filament 40 present, in turn, can be folded over itself, as in FIG. 1, forming the loop configuration 35, with the first and second ends 31, 32 extending therefrom. In this position, the shuttle 30 can be positioned through the hollow pathway 23 of the filamentary sleeve 20 such that at least a portion of the loop configuration 35 is positioned outside the pathway 23 at the first end 21 of the filamentary sleeve, and the first and second ends 31, 32 extend through the pathway 23 and out past the second end 22 of the filamentary sleeve. The shuttle 30 may be positioned as such, for example, by the use of a separate length of wire or suture (not shown) positioned through the pathway 23 and having a loop or hook on one end. The shuttle 30 may be engaged with the loop or hook and pulled into and through the sleeve 20 to a position as illustrated in FIG. 1. One example of such use of a loading wire or suture is illustrated in the heretofore referenced '586 and '592 applications, incorporated by reference herein.

FIG. 1 also illustrates the length of repair filament 50 having first and second free ends 51, 52. As discussed in detail below, the length of repair filament 50 and/or plurality of repair filaments 50 are used to engage the soft tissue (as in FIG. 4a), or otherwise apply tension or force to soft tissue, and secure tissue by similarly engaging the filamentary sleeve 20 in a manner which does not require any knots.

It is preferred, as illustrated in FIG. 1 and throughout this disclosure, that the filamentary sleeve 20 be constructed of a filament which has a larger inner diameter than an outer diameter of the filamentary shuttle 30, and that the shuttle 30 has a larger outer diameter than either of the inner filament 40 and the length of filament 50. Moreover, the inner diameter of the passageway 33 of the shuttle should be equal to or greater than the outer diameter of the inner filament 40. Furthermore, the diameter of the length of filament 50 may be about one half or less of the diameter of the hollow pathway 23 of the sleeve 20, which may allow for simplified maneuvering of the filament 50, relative to the sleeve 20, during manipulation in the various methods described below. However, such sizes may be dependent upon the desires of the operator and whether a tighter or looser fit is desired between the various filamentary elements of the present invention. In one example, the filamentary shuttle 30 may be #5 suture, the inner filament 40, if present, may be #1 suture, and the length of repair filament 50 may be #2 suture (which is normally used for working or repair suture in the orthopedic field).

FIG. 1B illustrates another embodiment of a filamentary fixation device including a sleeve 120 and a filamentary shuttle 130. It should be understood that either sleeve 20, 120 may be used with either shuttle 30, 130, or any variations or combinations thereof. Sleeve 120 includes first and second ends 121, 122, similar to shuttle 20, though shuttle 120 also includes first and second openings 126, 127 through which the shuttle 130 may be positioned such that, between openings 126, 127, the shuttle 130 is positioned outside of pathway 123. As discussed in the various incorporated references, cited above, positioning the shuttle 130 in this manner can reduce the overall size of the filamentary construct (i.e., sleeve and shuttle) on the end of an inserter (as in FIG. 2) thereby allowing the construct to be positioned in a smaller bone hole or otherwise to be more easily maneuvered in small spaces, such as through a cannula. Specifically, with shuttle 130 positioned outside of sleeve 120 at the point where the construct is folded onto an instrument allows the sleeve and shuttle to be vertically stacked on an inserter separately rather than being an integrated body The filamentary shuttle 130 illustrated in FIG. 1B differs from shuttle 30 in that shuttle 130 is not folded onto itself (see FIG. 1A versus FIG. 1B) and thus the shuttle 130 is positioned through the sleeve 120 such that a first end 131 is positioned outside one end 122 of the sleeve 120 while the second end 132 is positioned outside the other end 121 of the sleeve 120. FIG. 1B also illustrates how an inner filament 40 would be positioned in such a shuttle 130. In this embodiment, inner filament 40 is double over onto itself and positioned through at least a portion of passageway 133 through sleeve 130. Inner filament 40 may extend out through second end 132 of shuttle 130 to form a structure for engaging filament 50, such as a loop structure exemplified by eyelet 45. Alternatively, eyelet 45 of this embodiment could also be formed by passing the inner filament through the sidewall of the sleeve 130, towards second end 132, in similar fashion as is illustrated in FIG. 1A. While the sizes of the various filaments of FIG. 1B can vary as desired, similar to FIG. 1A, in a preferred example the shuttle 130 may be #7 suture, the inner filament 40, if present, may be #1 suture, and the length of repair filament 50 may be #2 suture. Of course, shuttle 130 may be larger than shuttle 30 since shuttle 130 is not being doubled over within the filamentary sleeve.

The embodiment of FIG. 1B is preferred for a few reasons. Having a shuttle 30 that originates as a straight filament as seen in FIG. 1B rather than the folded over configuration shown in FIG. 1A could offer the advantage of minimizing the risk of the shuttle becoming tangled or inadvertently ensnaring other filaments, tissue, or surgical equipment that are adjacent to it during various steps of a surgical procedure such as engaging of filament 50 and subsequent passing or shuttling of filament 50, particularly through a cannula in arthroscopic applications.

It should be noted that while the sleeve 120 and shuttle 130 of FIG. 1B is a preferred embodiment, and can be used in any of the illustrated and envisioned embodiments of the present invention, sleeve 20 and shuttle 30 will be illustrated and used in the exemplary embodiments herein for reasons of clarity and simplicity.

Figure 2:
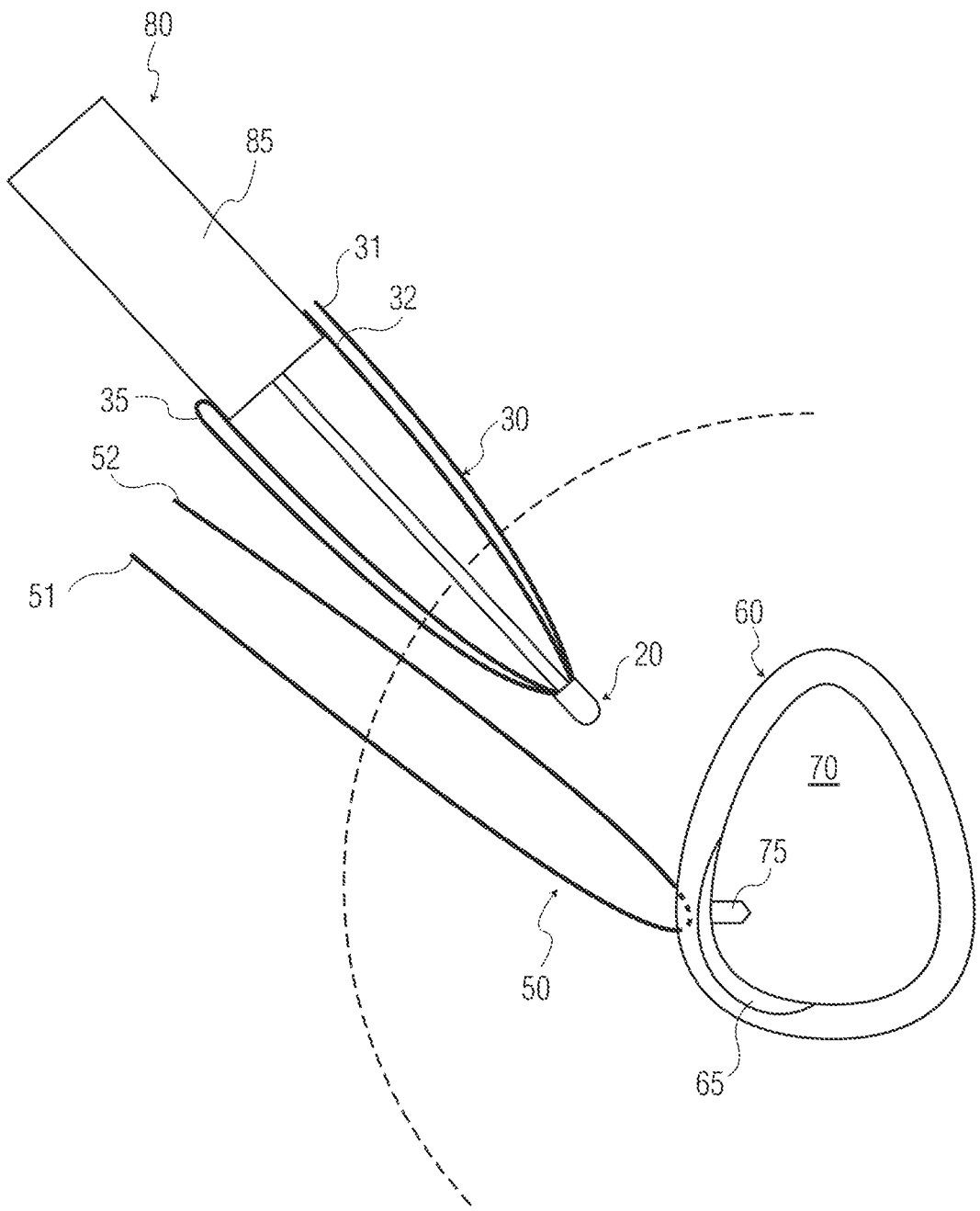
FIG. 2 illustrates the filamentary assembly of FIG. 1A, positioned on an instrument for an exemplary use for the repair of torn labrum tissue.

FIG. 2 illustrates one embodiment of how the filamentary fixation assembly 10 can be used in conjunction with an instrument 80. As illustrated, the sleeve 20 is folded around a distal end of the instrument, which has a shape of a blunt end, flat end, or a "field goal" post (i.e., the sleeve fits between the "goal posts"). When positioned on the instrument, the filamentary shuttle 30 should be sufficiently long such that both the loop configuration 35 and the first and second ends 31, 32 can extend proximally to or towards the handle 85, and can be held at such a position by the operator or by some connection point on the instrument 80. As will be discussed below, positioning the shuttle 30 in such a manner is useful for the operator, particularly for arthroscopic applications. The instrument 80 may be used to position the filamentary assembly 10 in a specific anatomical location, such as towards and into a bore hole 75 in a bone 70, e.g., as illustrated, a bore hole in a glenoid for the repair of labrum tissue 60. Potential instrumentation for use with the assembly, particularly for arthroscopic repairs, would also include a cannula (an example of which is illustrated in FIG. 8B as cannula 88), as is known in the art for arthroscopic applications, through which the assembly 10 and instrument 80 would pass through to the surgical site in the anatomy. Such instrumentation, including exemplary instruments 80, cannulas 88 and the use thereof, are described in the heretofore referenced applications, such as the '586 and '592 applications, incorporated by reference herein. In one example, the cannula may have an inner diameter of about 3.3 mm, which may be suitable for insertion of either or both a 2.3 mm drill (to prepare a bore hole) and instrument 80 with assembly 10.

In another embodiment, the present invention is a system for the repair of tissue including the above assembly 10. The system may further include instrument 80 as well as additional instrumentation such as a cannula, a drill or reamer (not shown) for preparation of a bore hole in bone (if required), needles and/or trocars which may be used to position the length of filament 50 around or through tissue, and a loading wire or suture as discussed above for positioning the shuttle 30 within the sleeve (though, it is preferred that the shuttle 30 be positioned within the sleeve at time of manufacture, and thus would arrive at the operator packaged as such).

In a further embodiment, the present invention is a kit including at least one filamentary sleeve 20, at least one filamentary shuttle 30, and a plurality of lengths of filaments 50 (or filaments 150, or any combination of filaments 50, 150). The plurality of filaments 50 can vary in length, color, diameter, strength, or the like, or, they can be identical to one another. In one example, such a kit may be packaged and offered to operators as a kit for labrum repair, in which a plurality of filaments 50 may be used with a single sleeve 20 and shuttle 30 (packaged as a unit (as in FIG. 1), or separate.

Such a kit may also include, for example, a plurality of sleeves 20 and shuttles 30 of varying length, width, material, color, or the like, or of identical characteristics. Such a kit could also include various configurations of sleeves 20, 120 (or other variations) and shuttles 30, 130 (or other variations) from which an operator can select the best types for a particular surgical procedure. Optionally, some or all of the plurality of shuttles can include an inner filament 40, and thus, a filamentary eyelet 45. In one further example, a variation of a kit could include a plurality of sleeves of various sizes, and at least one shuttle, which could be used, for example, for larger labrum tears which require multiple reattachment points on both the glenoid and labrum.

In another embodiment, a kit of the present invention may be specific to, for example, meniscal repair, and would include a plurality of filamentary sleeves 20 positioned on a single filamentary shuttle 30 or, alternatively, each on an individual filamentary shuttle 30. The kit can also include at least one length of repair filament 50, and thus, the filament 50 may be used with all of the sleeves 20 together (e.g., the sleeves operate as multiple "back stops" for multiple passes of the filament 50 through the meniscus tissue), or a single filament 50 can be provided for use with each sleeve 20 individually.

Such kits can also include additional components, such as at least one instrument 80, as well as additional instrumentation such as a cannula, a drill or reamer (not shown) for preparation of bore hole in bone (if required), needles (particularly for meniscus repair) and/or trocars which may be used to position the length of filament 50 around or through tissue (or, for example, through meniscus tissue and a tear through the meniscus tissue), and a loading wire or suture as discussed above for positioning the shuttle 30 within the sleeve (though, it is preferred that the shuttle 30 be positioned within the sleeve 20 at time of manufacture, and thus would arrive at the operator packaged as such).

While filamentary fixation devices, assemblies, systems and kits are preferred, it is also envisioned that other fixation devices, other than filamentary fixation devices such as filamentary sleeve 20, 120, can also be used in any of the devices, systems, kits and assemblies and methods of use and assembly described or envisioned herein. For example, a tubular, flexible, plastic implant can replace the sleeve and be used. Alternatively, traditional suture anchors (as in FIG. 11A-C) could also be used.

Certain exemplary embodiments of methods of assembly and use will now be described. While such methods will be described in terms of a repair and reattachment of labrum tissue 60 to a glenoid 70, it is envisioned that the assembly of the present invention may be performed in other anatomical locations and for other anatomical repairs such as, for example, acetabular labral repair, meniscal repair, rotator cuff repair, and the like. Similarly, it is envisioned that the filamentary fixation devices, assemblies and systems of the present invention may also be used in bone-bone repair such as reducing fractures, reattaching bone fragments and chips to bone, and for the repair of bone-bone joints such as the acromioclavicular joint. However, for ease of reference, the methods of assembly and use will be directed towards the repair of soft tissue using the filamentary fixation assembly 10, and specifically, the deployment of the filamentary sleeve 20 into a bore hole 75 in the glenoid 70 for repair and reattachment of labrum tissue 60, unless stated otherwise.

It should be understood that FIGS. 3A-8A and 9A-9B illustrate certain embodiments of methods of assembly and use as a close-up, simplified illustration. FIG. 8B, on the other hand, provides an illustration of how any of these particular methods would likely be performed in an actual arthroscopic surgical method—i.e., through a cannula 88, with many of the filament manipulation steps occurring outside of the surgical site in plain view of the operator. It should be understood that FIGS. 3A-8A and 9A-9B are presented in such a way merely for the sake of clarity and that each of the illustrated steps can and, in a preferred embodiment should, be performed through a cannula, as in FIG. 8B.

Generally, the present invention, in one embodiment, includes a method of securing tissue including passing or positioning a length of filament 50 around or through tissue to be secured, implanting a filamentary sleeve 30 into an another tissue (such as bone, another portion of the tissue to be secured, other adjacent tissue, or the like) and passing at least a portion of filament 50 through the sleeve to form a one-way cleat. As will be described below, the one-way cleat secures the tissue, through filament 50, to the filamentary sleeve and the another tissue. In a specific example, the filament 50 is positioned around or through a labrum tissue and the filament sleeve is positioned in the glenoid, such that the assembly of the filament and sleeve secures the labrum tissue to bone.

Figure 3A:
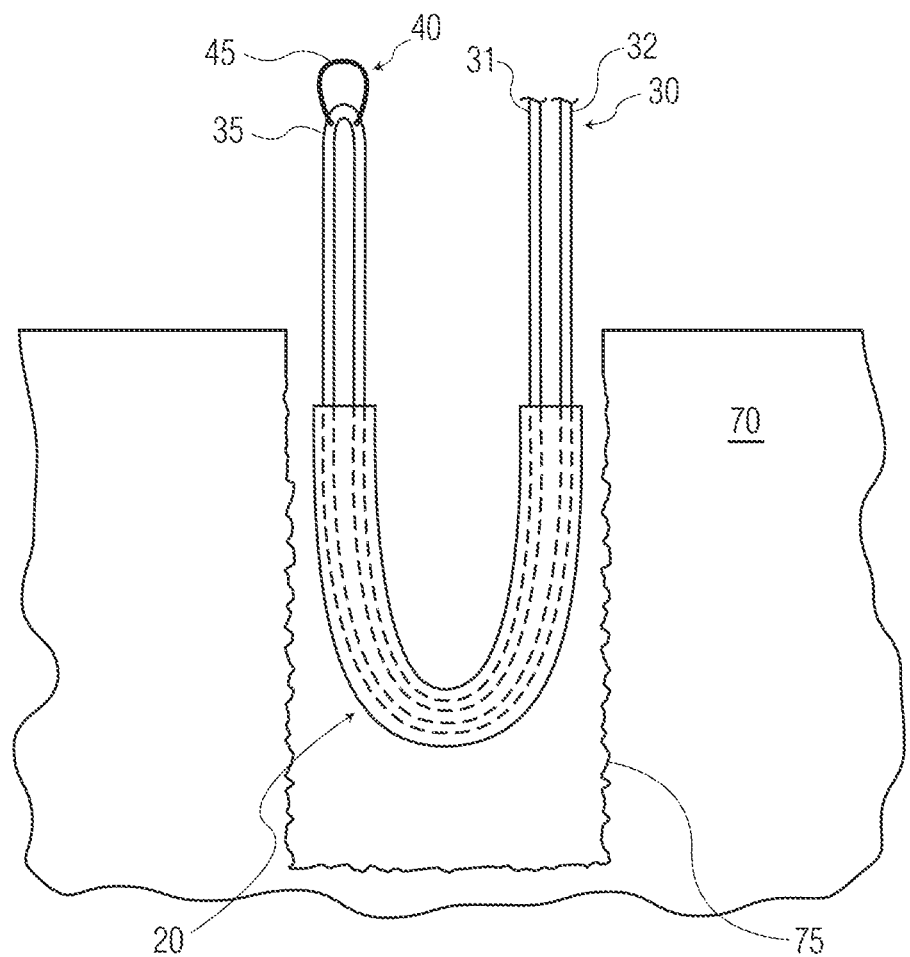
Figure 3B:
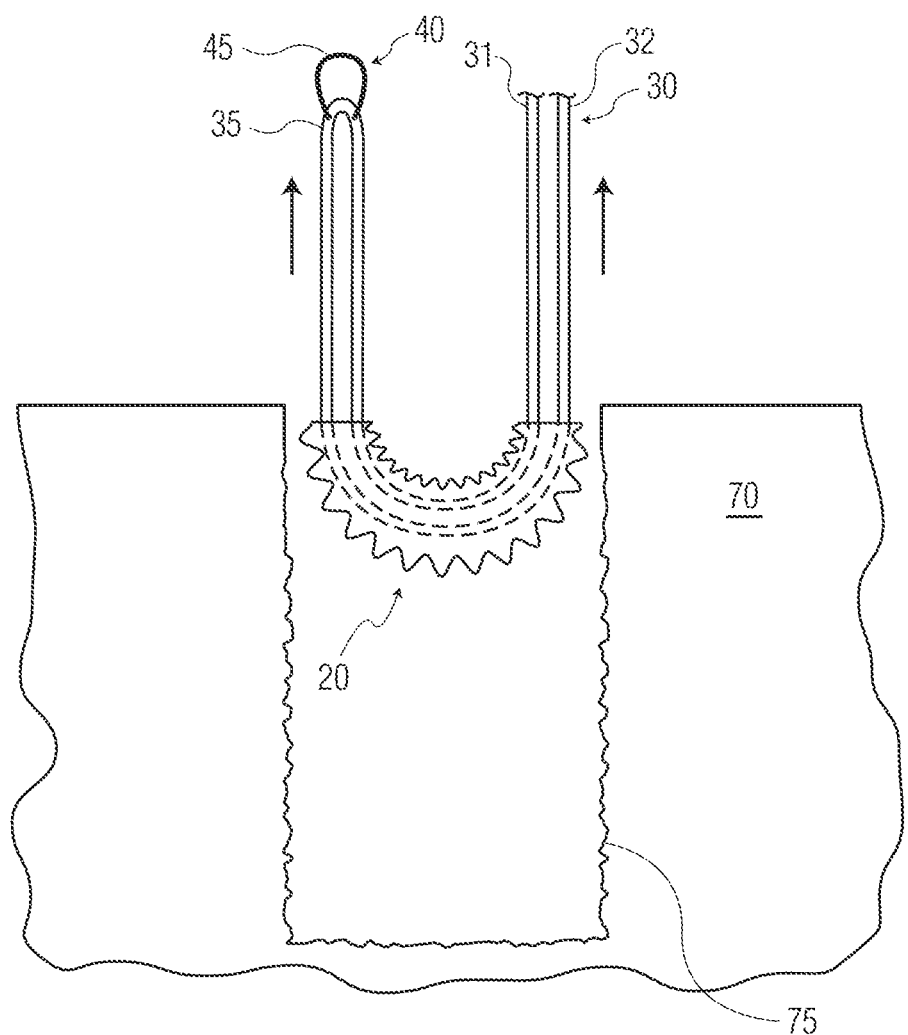
FIG. 3B illustrates the assembly deploying to a second configuration.

FIGS. 3A and 3B illustrate one embodiment of a method of repairing tissue of the present invention. Specifically, FIGS. 3A and 3B of positioning of the assembly 10, specifically the filamentary sleeve 20. As will be discussed further below, while the preferred embodiment of the present invention includes placement of the assembly 10 into a bore hole 75 in a bone 70, the assembly may be positioned in other anatomical locations other than within a bone.

Continuing with this embodiment, FIG. 3A illustrates (with the surrounding soft tissue and instrument 80 removed for clarity) the initial positioning and a filamentary sleeve 20, with filamentary shuttle 30 therein, into the bore hole 75 in the bone 70. For example, the bone may be a glenoid, and the bore hole 75 may be at an anatomical position for reattachment of torn labrum tissue 65 thereto. FIG. 3B illustrates deployment of the sleeve 20 within the bore hole 75. Such deployment is achieved by the operator grasping and tensioning, in a proximal direction, the first and second ends 31, 32 and the loop configuration 35. Such deployment of the sleeve 20 renders the sleeve 20 fixedly secured within the bore hole such that the filamentary shuttle 30 may be used to pass the length of filament 50 therethrough while the sleeve remains within the bore hole 75. Of course, such deployment may alternatively be only a partial deployment wherein the sleeve 20 partially deploys, and as such, the sleeve is removeably secured within the bore hole. However, from a practical standpoint, it is preferred that the operator fully deploy the sleeve 20 such that, during the tensioning step of the filament 50 and tissue 60, the sleeve 20 does not inadvertently exit the bore hole, though it is appreciated that the tensioning of the filament 50 and tissue 60 may result in additional deployment (e.g., crushing or bunching of the sleeve 20, or possible movement of the sleeve relative to the surrounding bone). Such deployment is discussed further in the heretofore referenced applications incorporated by reference herein.

With the filamentary sleeve 20 in the bore hole 75, and deployed towards or into the second configuration (FIG. 3B), the sleeve 20 is now ready for engagement with the length of filament 50. The length of filament, either before or after implantation of the sleeve 20, is passed around or through the soft tissue 60, and specifically through the tissue at or adjacent to tear 65, as in FIG. 4A, such that the first and second free ends 51, 52 extend from the tissue 60. If desired, the filament 50 could be passed through tissue more than once; for example, passed twice to create what is commonly called a mattress stitch. Continuing with the example of an arthroscopic repair, the ends 51, 52 should be brought outside the surgical site and to the loop configuration 35 of the filamentary shuttle which is also already positioned outside the surgical site (as is was originally positioned adjacent handle 95 of instrument 80, though by this point in the procedure, typically prior to deployment of sleeve 20, the inserter is removed from the cannula and surgical site). The ends 51, 52 may then be engaged with the shuttle 30, such as by being passed through a loop structure, such as the loop configuration 35 or alternatively, if present, the filament eyelet 45 of the inner filament 40. Of course, if shuttle 130 and were used in this method, the filament ends would be engaged by the eyelet 45 as this embodiment does not include a separate loop configuration on the sleeve 130 itself.

Figure 4A:
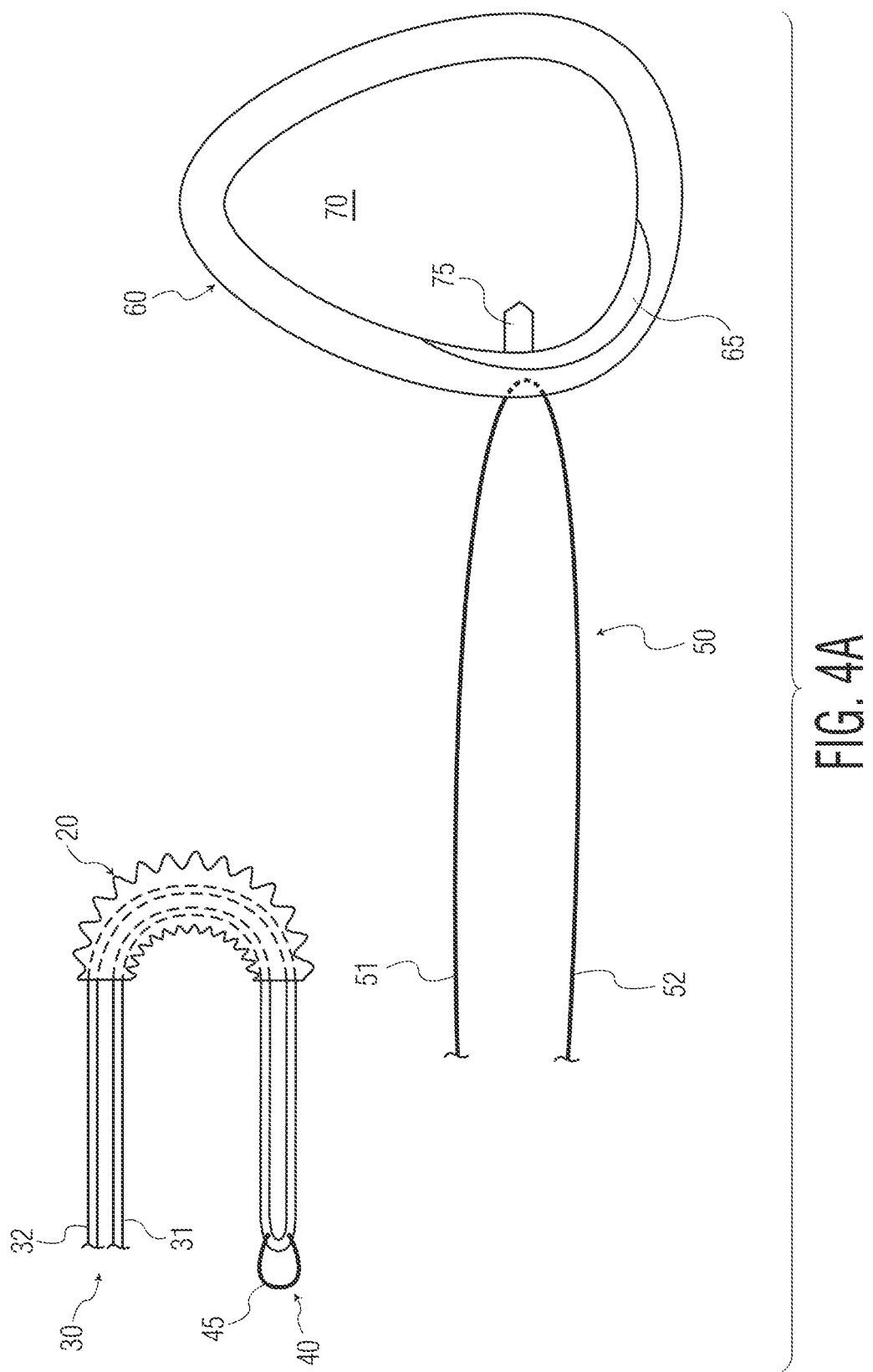
FIG. 4A illustrates a representative use of one embodiment of a filamentary assembly or system for the exemplary use for the repair of torn labrum tissue.
Figure 4B:
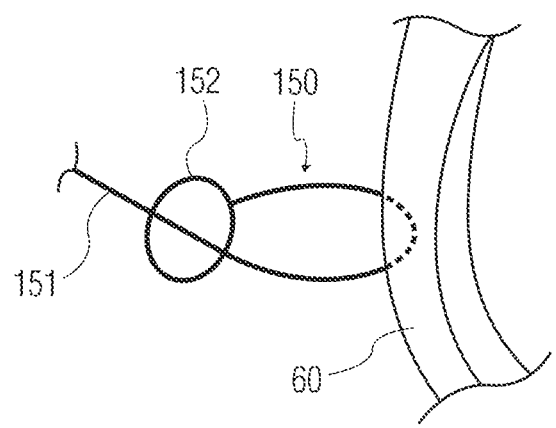
FIG. 4B illustrates a close-up of another embodiment of one aspect of the filamentary assembly or system.

In one alternative embodiment, illustrated in FIG. 4B, the length of filament 150 may include a loop 152 on one free end of the filament. As illustrated, the loop 152 may be used in such a way that the filament 150 may be passed through or around tissue 60, and free end 151 may be passed through the loop 152 and tensioned to draw the loop 152 against the tissue 60 in a "luggage tag" configuration. Of course, in this instance, the filament 150 would only have one end 151 extending from the tissue rather than two ends 51, 52 as when the filament 50 is used. However, a filament 150 including two lengths of filament extending from the loop 152 may also be used to provide the operator with two free ends even when a luggage tag arrangement is used. Examples of such filaments are disclosed in U.S. application Ser. No. 13/441,290, filed Apr. 6, 2012, the entirety of which is incorporated by reference herein as if fully set forth herein, and which is assigned to the same entity as the present application.

Figure 5:
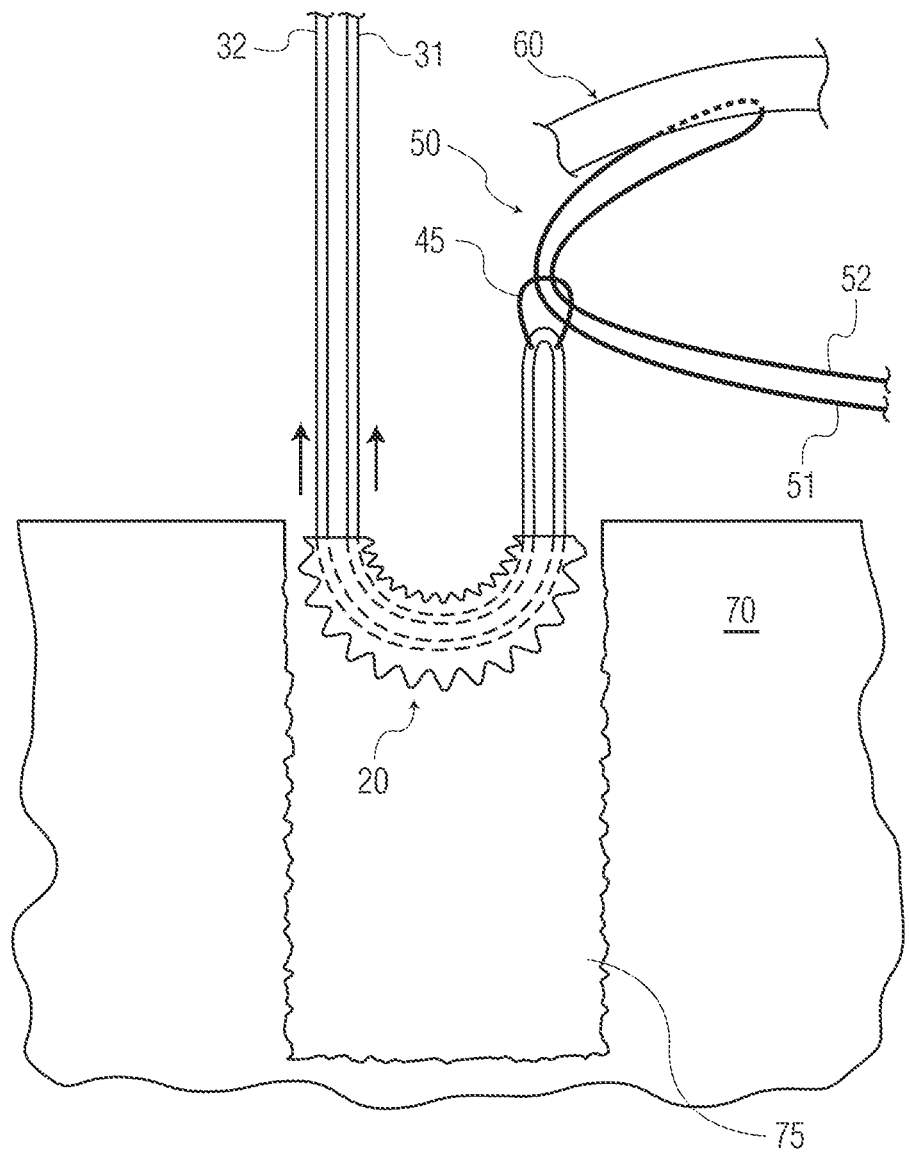
FIG. 5 illustrates a step of one embodiment of a method of use or assembly.

Regardless of which length of filament 50, 150 is used (and continuing as to the length of filament 50 for discussion purposes), FIG. 5 illustrates, in representative fashion only, passing the first and second free ends 51, 52 through the filament eyelet 45. As it is preferable to have the loop configuration 35 or filament eyelet 45 adjacent the handle 85 of the instrument 80, this step may be preformed outside of the surgical site (though instrument 80 is typically removed at this point) such that the free ends 51, are brought outside the surgical site to the loop configuration 35 or filament eyelet 45. However, it is envisioned that this step, or any of the steps of this method, may alternatively be performed within the patient and at the surgical site with the assistance of an endoscope or other viewing instrumentation as known in the art.

Figure 6:
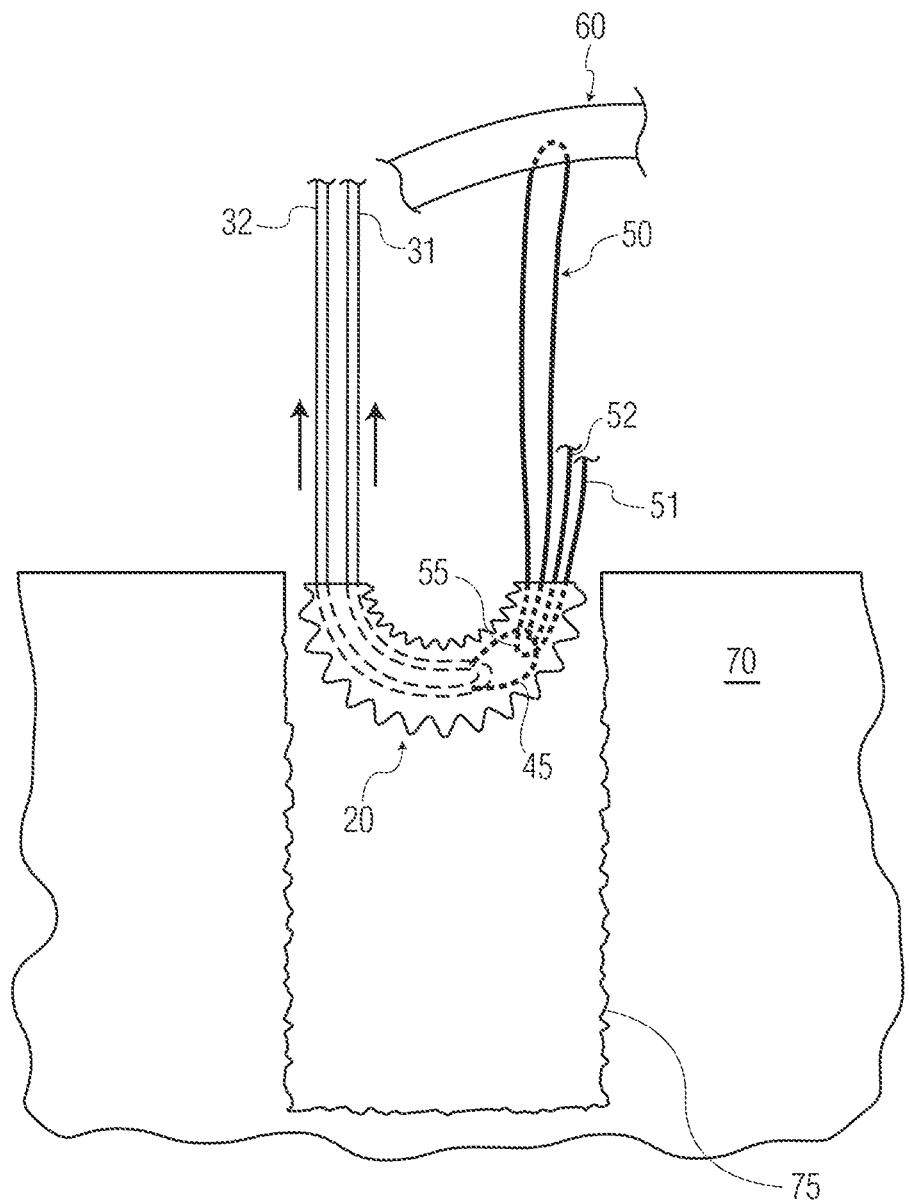
FIG. 6 illustrates another step of the method embodiment of FIG. 5.

FIG. 6 illustrates the next step of drawing the length of filament 50 into the filamentary sleeve 20 by pulling on the filament end 31, and 32 (specifically as to shuttle 30), of the shuttle 30 (and ends 41, 42 of inner filament 40, if present). As the loop configuration 35 or filament eyelet 45 travels through the sleeve 20, a second loop configuration 55 is formed on the length of filament, wherein in this position, the length of filament is folded over itself and is positioned through the sleeve such that at least a portion of the second loop configuration 55 is positioned outside the sleeve at end 22 of the filamentary sleeve, and the two or more filament free ends 51, 52 extend through the sleeve. Continuing with the example of an arthroscopic surgical procedure, the length of filament 50 may have a sufficient length such that the second loop configuration 55 as well as the two filament free ends 51, 52 may extend out of the surgical site proximally through a cannula (if present, see FIG. 8B), and to the operator, though alternatively, even in arthroscopic procedures, the loop and free ends may remain within the surgical site.

With the filamentary sleeve 20 fully deployed prior to this step, it is noted that, commonly, the pathway 23 crushes or compresses along with the entirety of the sleeve 20 as the sleeve deploys (FIG. 3B). Such compression may make it difficult to slide filaments through the pathway 23. In light of this potential issue, the filamentary shuttle 30 has an equivalent or preferably a larger diameter than the folded length of filament 50 (as discussed above, and also shuttle 130 would similarly have a larger diameter than filament 50). The differences in thickness allow the shuttle 30 to act as a larger placeholder within the pathway 23 during deployment, such that a suitably sized pathway can be preserved to provide for simplified passing or shuttling of the filament 50 through the sleeve 20, particularly since both ends 51, 52 of the filament 50 will be doubled over themselves and passed through the sleeve 20 (unless filament 150 is used, in which case only a single free end 151 would be doubled over itself). Similarly, the use of the inner filament 40, and eyelet 45, may also provide for simplified passing of the filament 50 into and through the sleeve because, with the filament 50 wrapping around the eyelet 45 rather than the loop configuration 35, a smaller diameter at the intersection of the filament 50 and inner filament 40 is maintained. This benefit may also be realized relative to shuttle 130, which, while not folded onto itself, still has a large diameter.

Figure 7A:
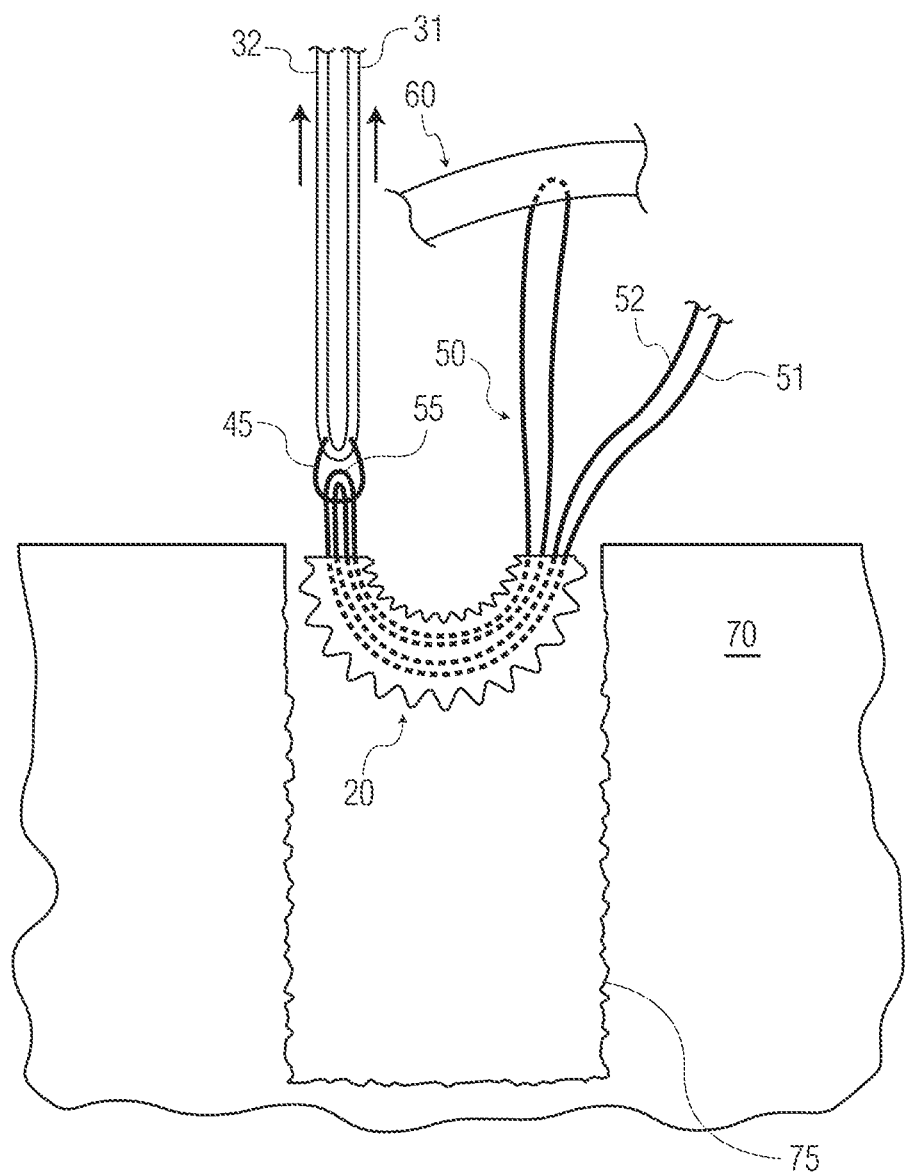
FIGS. 7A and 7B illustrate an additional, optional step of the method of FIGS. 5 and 6.
Figure 7B:
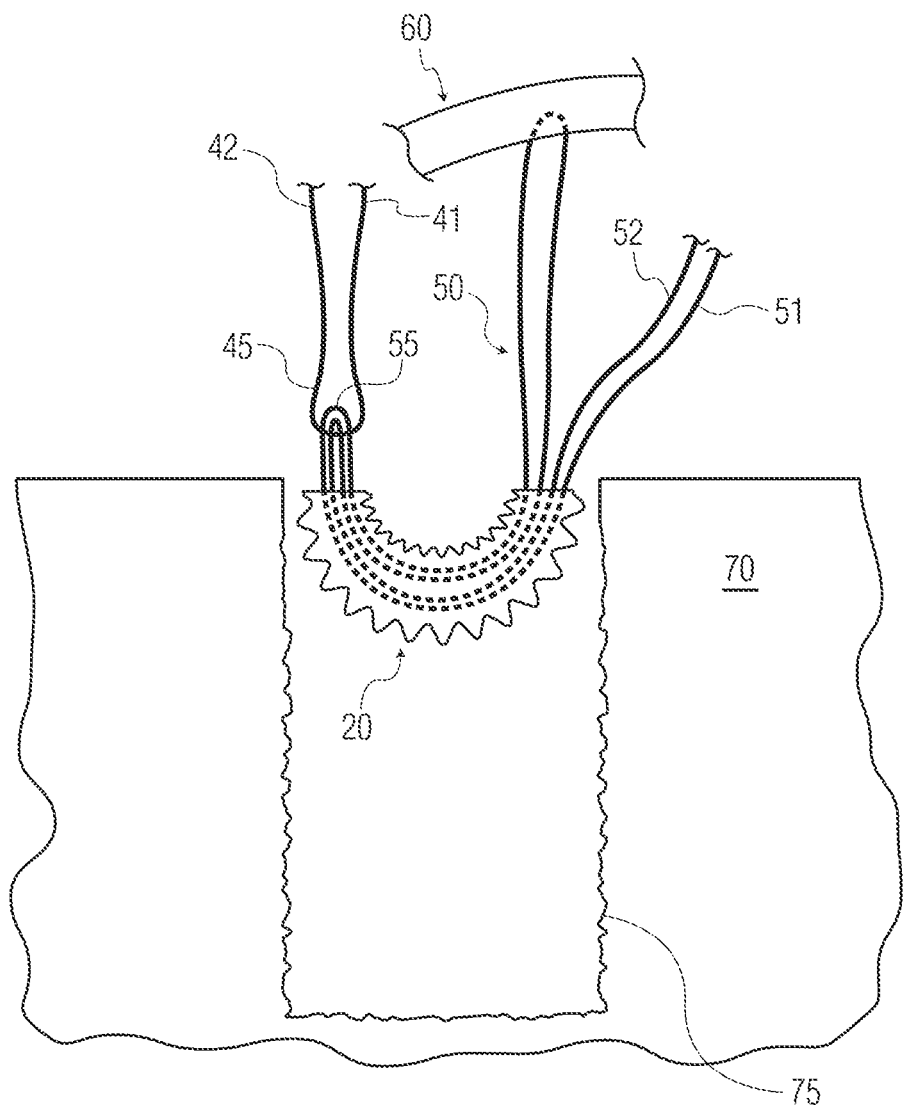

FIGS. 7A and 7B illustrate an optional step performed if the inner filament 40 is used (again, these steps apply equally to both examples of sleeve 30, 130 illustrated in FIGS. 1A and 1B). Following the positioning of the length of filament 50 through the filamentary sleeve 20, the filamentary shuttle 30, or outer filament, may be separated from the inner filament 40 such that the inner filament 40 can be removed from the second loop configuration 55. Alternatively, the inner filament may be simply cut, or, if ends 41 and 42 are accessible (i.e., projecting from openings 38, 39), the operator may simply pull on one of the ends 41, to slide the inner filament 40 from the shuttle 30 and second loop configuration 55.

Figure 8A:
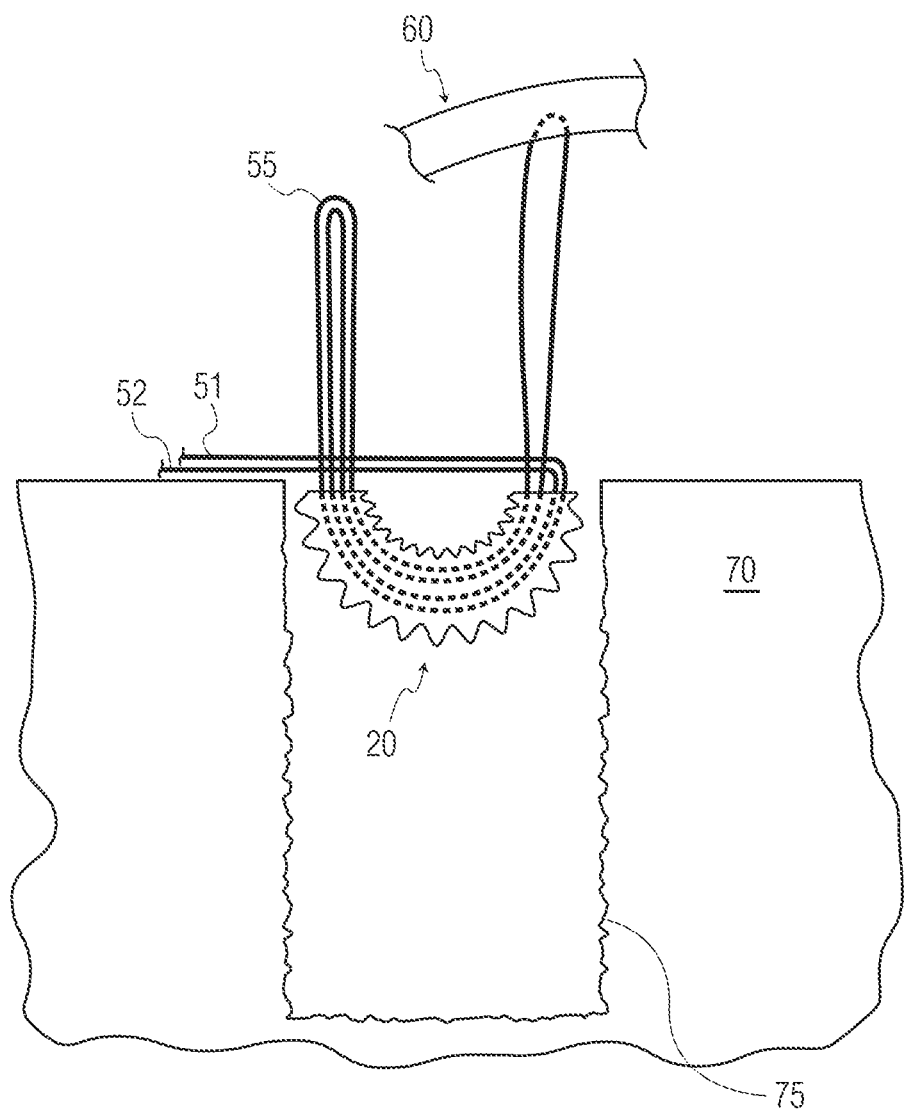
FIG. 8A illustrates yet another step of the method of FIGS. 5-7.
Figure 8B:
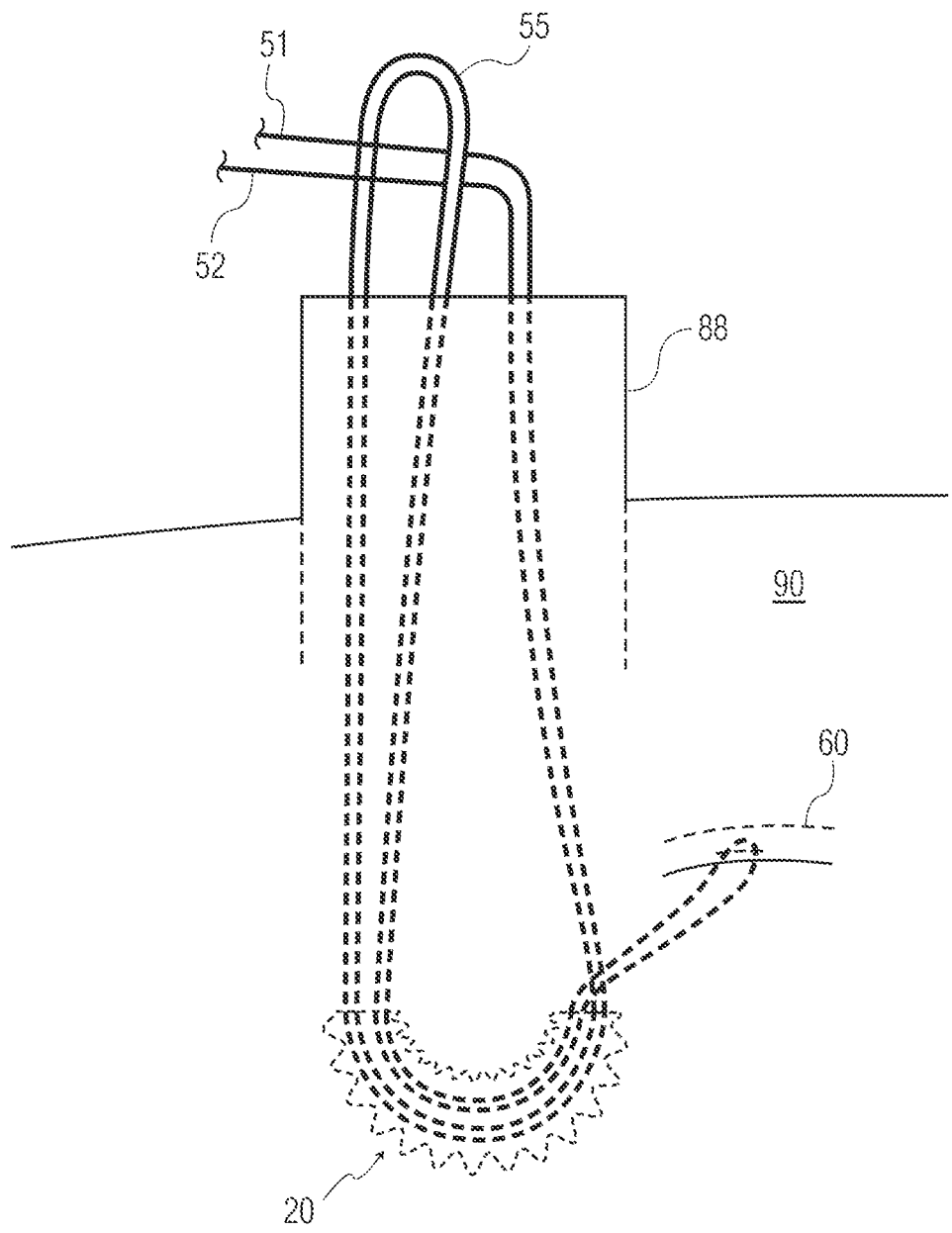
FIG. 8B is a representative view of the step of FIG. 8A illustrating how such a method would be performed through a cannula during arthroscopic repair.

Regardless of whether the inner filament 40 is used, FIGS. 8A and 8B illustrate the next step once the filamentary shuttle 30, and optionally inner filament 40, is removed from the second loop configuration 55. Again, the second loop configuration may remain within the surgical site or may extend proximally outside of the surgical site and towards the operator, as in FIG. 8B, which is preferred. In either situation, the free ends 51, 52 of the length of filament 50 are then maneuvered through the second loop configuration 55. Such a configuration would also allow for multiple filaments to be positioned in this fashion. Alternatively, if filament 150 (or multiple filaments 150) is used, only a single free end 151 of each filament 150 will be passed through a second loop configuration 155.

As noted above, FIG. 8B provides a representative view of how this embodiment of the method can be performed in an arthroscopic surgical procedure, with the steps being performed outside of the surgical site, and further, any of the other steps of this embodiment, as have been described, can also be performed through a cannula 88 as in FIG. 8B.

Figure 9A:
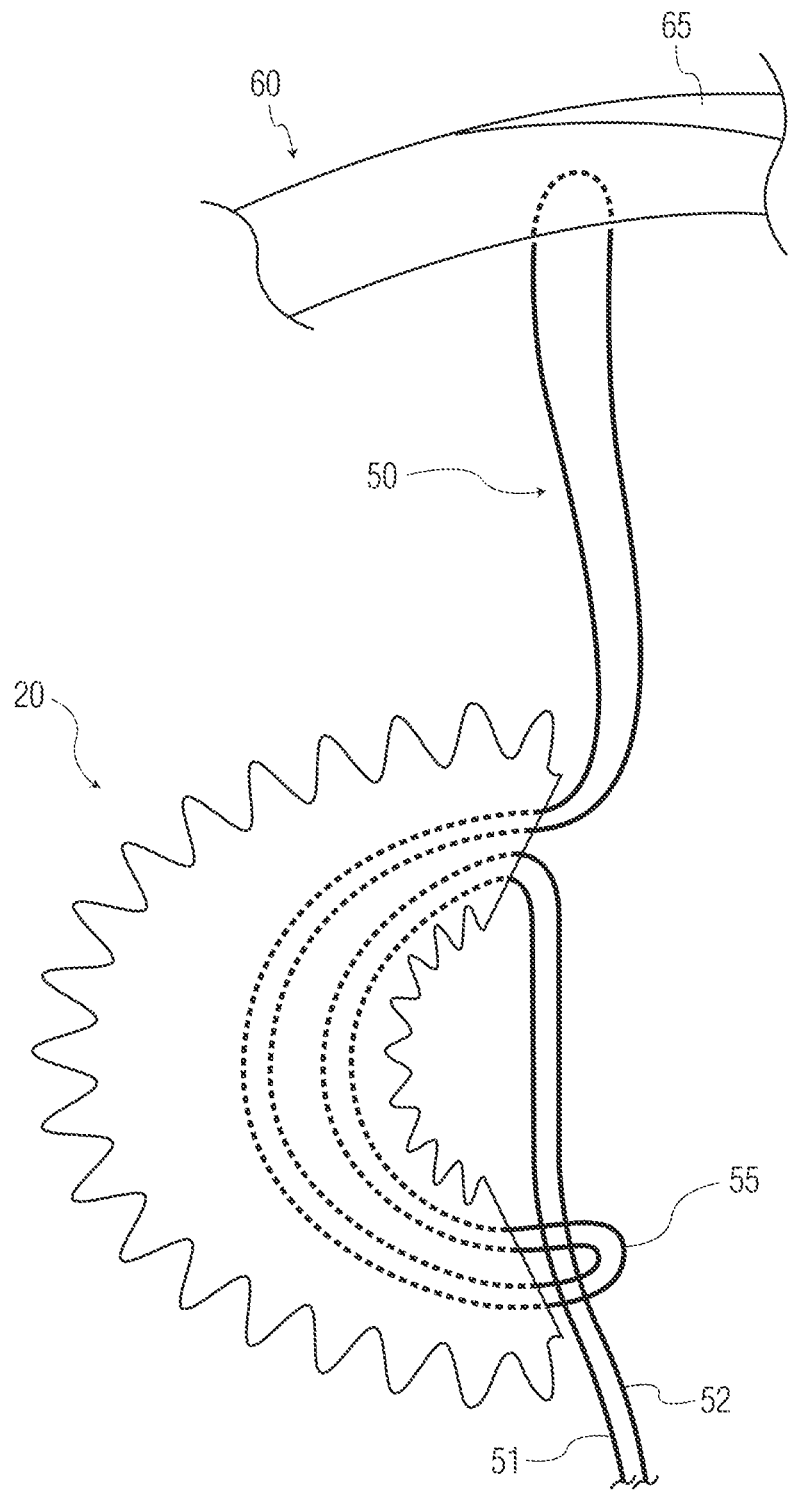
FIG. 9A illustrates yet a further step of the method of FIGS. 5-8.

FIG. 9A illustrates the completed configuration of assembly 10 in which the tissue 60 is secured, reattached, or the like. In maintaining the example of labrum tissue repair, the completed configuration of the assembly 10, within the glenoid, secures the labrum back against the surface of the glenoid to compress the tear 65. Specifically, the free ends 51, 52 (together or alternating by cycling between one free end and the other) are tensioned such that the second loop configuration 55 travels towards and into the pathway 23 of the filamentary sleeve 20, the length of filament 50 applies tension to the tissue 60, and the free ends, passed through the second loop configuration, are secured within the second loop configuration. Optionally, the second loop configuration may be forced towards and into the pathway 23 of the filamentary sleeve 20 with a knot pusher or the like, or by pulling the free ends 51, 52 apart from each other. The second loop configuration, as tensioned, effectively forms a one-way cleat such that the free ends 51, 52 may be tensioned further, but any tension applied on the assembly by the tissue 60, i.e., in a direction opposite the free ends 51, 52, would only force the second loop configuration into or up against the sleeve 20 and thereby prevent the free ends 51, 52 from loosening.

Figure 9B:
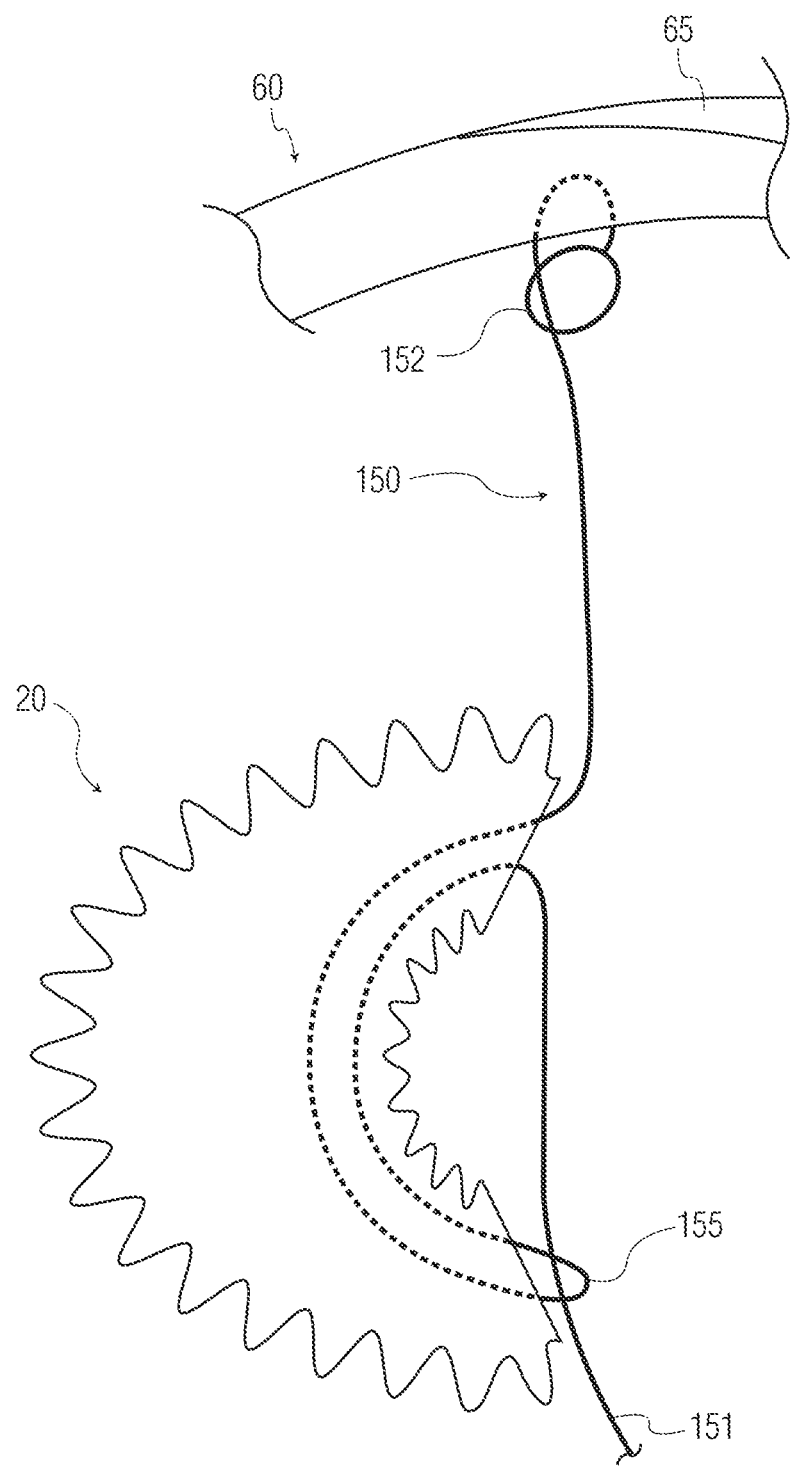
FIG. 9B illustrates a step of a method of use or assembly utilizing a filamentary assembly or system, a portion of such assembly or system illustrated in FIG. 4B.

Similarly, FIG. 9B illustrates the completed configuration of assembly 10 in which the tissue 60 is secured, reattached, or the like, as above, though including the length of filament 150 (or filaments 150) rather than filament 50. Similar to the assembly of FIG. 9A, the second loop configuration 155 as tensioned, effectively forms a one-way cleat such that the free end 51 may be tensioned further, but any tension applied on the assembly by the tissue 60, i.e., in a direction opposite the free end 151, would only force the second loop configuration into or up against the sleeve 20 and thereby prevent the free end 151 from loosening. The use of filament 151 may reduce the size of the overall repair, and possibly, even the size of the bore hole, as compared to the use of filament(s) 50.

It is envisioned that, if filament 150 is used, it would be easier to utilize multiple filaments 150 (not shown) which may be passed through the tissue 60 at multiple points, as desired based on the position, size and type of tear 65 to the tissue. Each of the filaments 150 may then be directed to the loop configuration 35 and positioned through a single sleeve 20 (or multiple sleeves of course) and tensioned as above. In another embodiment, such as in a rotator cuff repair, it would be common for multiple filaments 50 (2-4 such filaments 50, for example) to be shuttled through a single sleeve 20. For the glenoid repair described above, multiple filaments 50 could be used, though filaments 150 would be preferred as they each would include only a single free end 151 doubled over itself in the sleeve, and thus more filaments 150 may be positioned in a single sleeve 20 than filaments 50.

Following sufficient tensioning of the filament 50, 150, the excess portion of the filament free end 151, or ends 51, 52, may be cut away and the surgical site closed as is known in the art. Such an embodiment can achieve repair and attachment of soft tissue 60 without the need to tie any knots, and thus, the repair is simple to perform for an operator, is free of any knots which may loosen or come untied or interfere with anatomy, and is sufficiently strong to hold the soft tissue in place until the tissue 60 heals to the repair site.

Figure 10A:
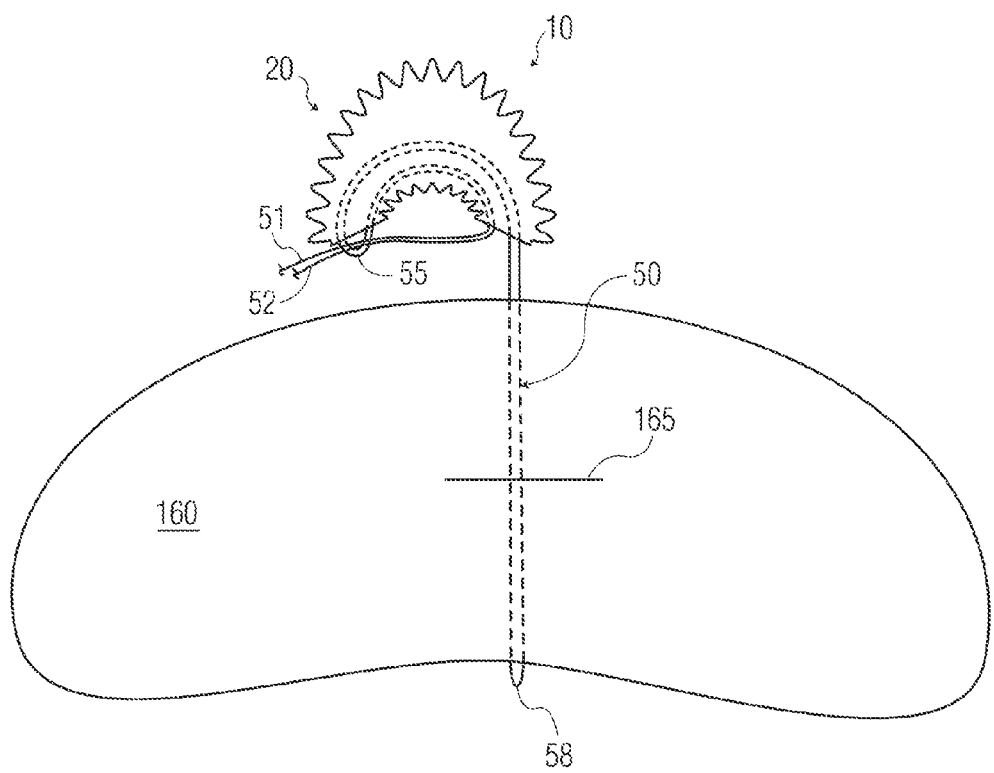
FIGS. 10A and 10B illustrate various embodiments of methods of use or assembly.

In one alternative embodiment, the result of which is illustrated in FIG. 10A, assembly 10 may be used to repair other types of soft tissue 160 whereby the filamentary sleeve 20 is not positioned within a bore hole in a bone, but instead is positioned merely to abut an edge or surface of a soft tissue to be repaired. Such a repair may be particularly useful in the repair of a tear 165 in meniscus 160, or alternatively, bone-bone applications to reduce one bone or fragment to another bone or fragment. Similar to the above embodiment, length of filament 50 is passed through the meniscal tissue, and through the tear 165, as is known in the art, to, preferably, an exterior side of the meniscus where the sleeve 20 will be positioned. The filament 50 is stabilized in the tissue by wrapping around the opposite edge of the tissue to form a u-turn 58. The u-turn may be buttressed using a back stop such as a button anchor, another sleeve 20, or other implant as is known in the art. The filament 50 may be positioned through the pathway 23 of the sleeve 20, as explained above, and the free ends 51, 52 may be tensioned to reduce the second loop configuration 55 and tension the tissue to compress the tear 165. As before, the second loop configuration 55 effectively forms a one-way cleat to secure the tissue, sleeve and filament to one another and complete the repair.

Figure 10B:
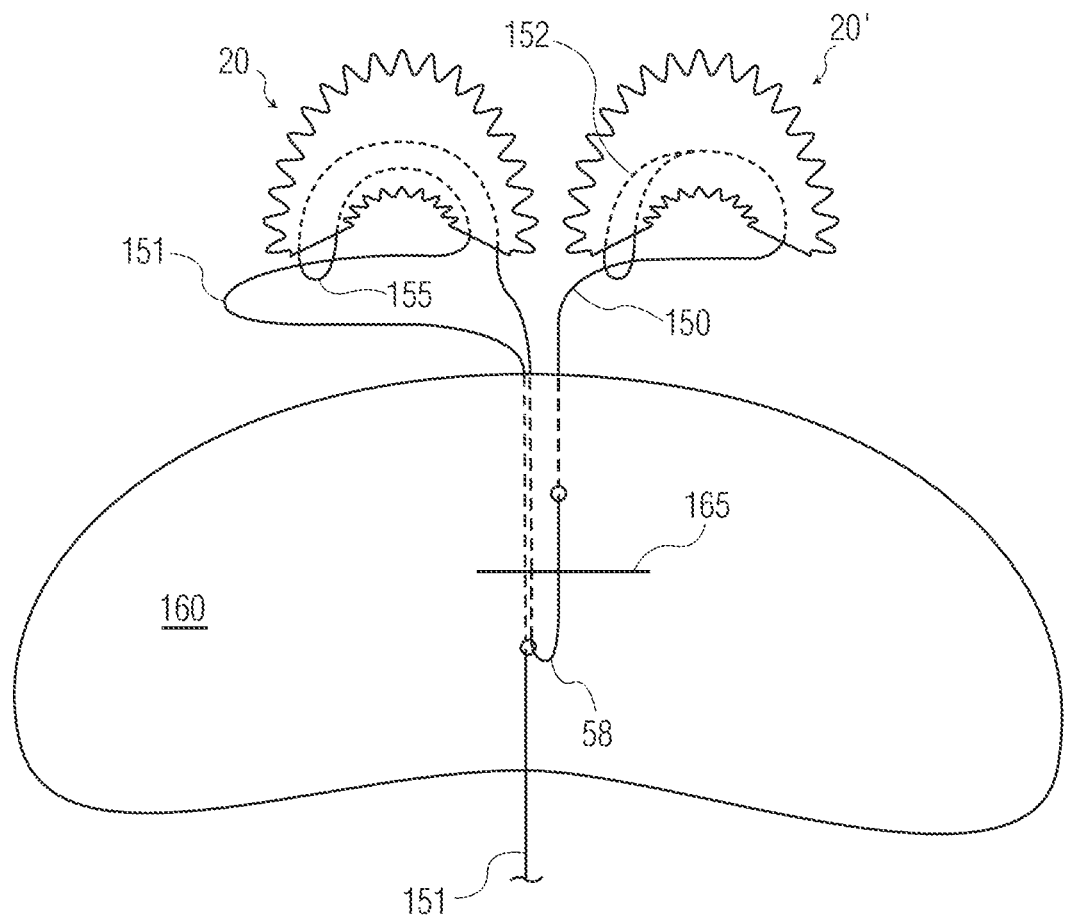

FIG. 10B illustrates an alternative embodiment where a second filamentary fixation device, filamentary sleeve 20', is inserted through the soft tissue and deployed on the exterior side of the meniscus, featuring an integrated filament 150 where end 151 is routed through a separate sleeve 20 as similarly shown in FIG. 9B. As illustrated, the loop 152 of filament 150 would be positioned through the sleeve 20' and the first free end 151 positioned through the loop would be tensioned to deploy sleeve 20' and secure the sleeve 20' against the external side of the meniscus. As in FIG. 9A, the free end 151 may then be passed through the meniscus in any configuration desired (either during the surgical procedure or pre-packaged with the desired filament routing). Illustrated is a preferred configuration, in which the free end 151 passes through the tissue to a position adjacent the tear 165, passing over the tear and re-entering the meniscal tissue at u-turn 58. The free end 151 can then navigate through the tear 165 and the tissue 160 to a second position and second sleeve 20. The filament may then be passed through sleeve 20 and a one-way cleat may be forms as described above. Optionally, and assuming the filament 150 has sufficient length, the free end 151 may pass through the meniscal tissue, and through tear 165, again and to a third or more sleeve, another backstop, tied into a knot, or the like. Also, of course, sleeve 20' may be replaced by another sufficient backstop structure, may be tied into a knot, or the like. In another alternative, the free end 151 and loop 152 may simply be positioned through the meniscus to form the "luggage tag" configuration as disclosed above, from where the free end 151 may then proceed to sleeve 20 or other anchor.

In a preferred embodiment, for example, the sleeves 20, 20' and filament 150 would be pre-fabricated such that both sleeves are positioned along the filament as illustrated in FIG. 10B. The sleeves would then be positioned on an instrument, such as an elongated needle, such that the needle may puncture the meniscus tissue in two places (illustrated as the two openings through which filament 150 pass) and deploy the two sleeves 20, 20' as shown. Once puncturing and positioning the two anchors, the free end 151 may simply be tensioned to deploy the two sleeves, form the one-way cleat with second loop configuration 155, and compress the meniscus tear 165 to complete the procedure. Essentially, such a method would remove the need for a operator to route the filament 150 through the tissue and through the sleeves. Instead, with the filament 150 already positioned through the sleeves, the needle instrument can simply puncture the tissue and position the sleeves as shown, which may result in a more efficient and reliable repair.

In another embodiment, the above method may be performed using a system including a filamentary fixation device including first sleeve 20, a second sleeve 20' and a filament 150, wherein the filament is positioned through at least a portion of the first sleeve and at least a portion of the second sleeve, and an instrument (not shown) adapted to deploy the filamentary fixation device to repair a tissue.

It is envisioned that multiple sleeves 20 may be used as necessary dependent on the position, size and type of tear in tissue amenable to such a repair. For example, using the aforementioned kit disclosed above, a single filamentary shuttle 30 may be positioned through multiple sleeves 20 (not shown), or multiple shuttles may be positioned through multiple sleeves, such that the filament 50, 150 (or filaments) can be positioned through the sleeves and secured within each one. One preferred configuration would include a sleeve at the sides of the tissue after each pass of the filament through the meniscus, such that each pass of the filament may be tensioned to compress the tissue along each pass.

Figure 12A:
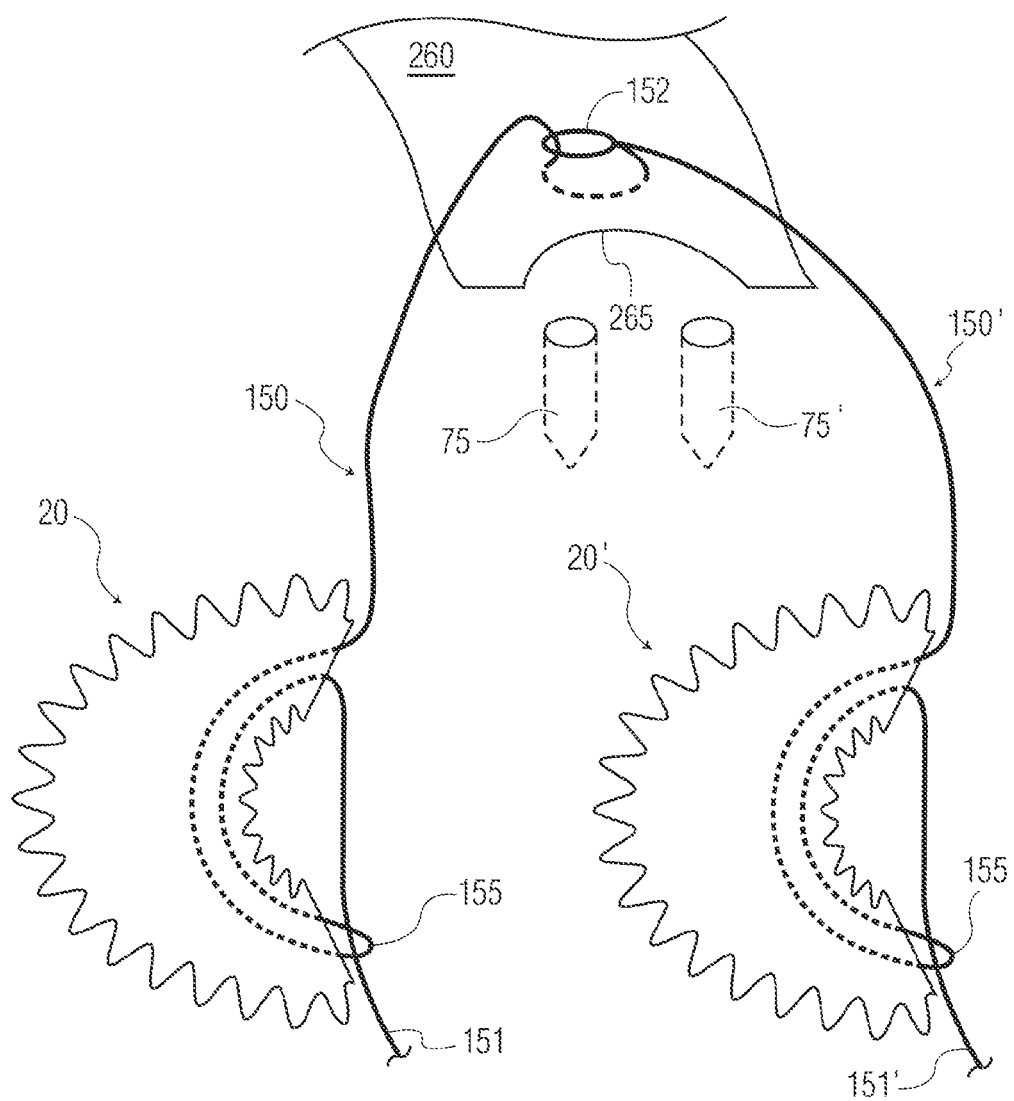
FIGS. 12A and 12B illustrate a further embodiment of a method of use or assembly.

In yet another embodiment, the present invention includes a method for the repair of a tissue, such as a rotator cuff. As illustrated in FIG. 12A, a filament 150 including two tails 151 and 151' extending from the loop 152 is positioned through tissue 260 in a "luggage tag" configuration, as discussed above. Such a filament, and configuration through tissue, is described in the '290 application incorporated by reference above. FIG. 12A illustrates one example where tissue 260 is a rotator cuff and 265 is a rotator cuff tear for ease of reference, though this embodiment is not limited to this anatomy.

From the "luggage tag" configuration, the first free end 151 is shuttled through a sleeve 20 as described above to create a one-way cleat with second loop configuration 155. During this step, sleeve 20 would be implanted and deployed in bore hole 75 (as described above) but is shown outside for clarity of the filament routing of the assembly. Then, the second free end 151' is shuttled through a second sleeve 20' as described above to create another one-way cleat. Again, during this step, sleeve 20' would be implanted in bore hole 75' (as described above) but is shown outside for clarity of the filament routing of the assembly. It should be noted that bore holes 75, 75' are considered lateral bore holes for rotator cuff repair, as known in the art. The two free ends 151, 151' would then be tensioned to apply tension to the rotator cuff which may pull the cuff laterally towards bore holes 75, 75'. Alternatively two separate and independent filaments 50 (or filaments 150 with a single tail each) could have been passed through the rotator cuff and secured to the two separate holes 75, 75' but the luggage tag offers additional tissue compression or engagement with the same amount of filament passing steps through the rotator cuff tissue.

Figure 12B:
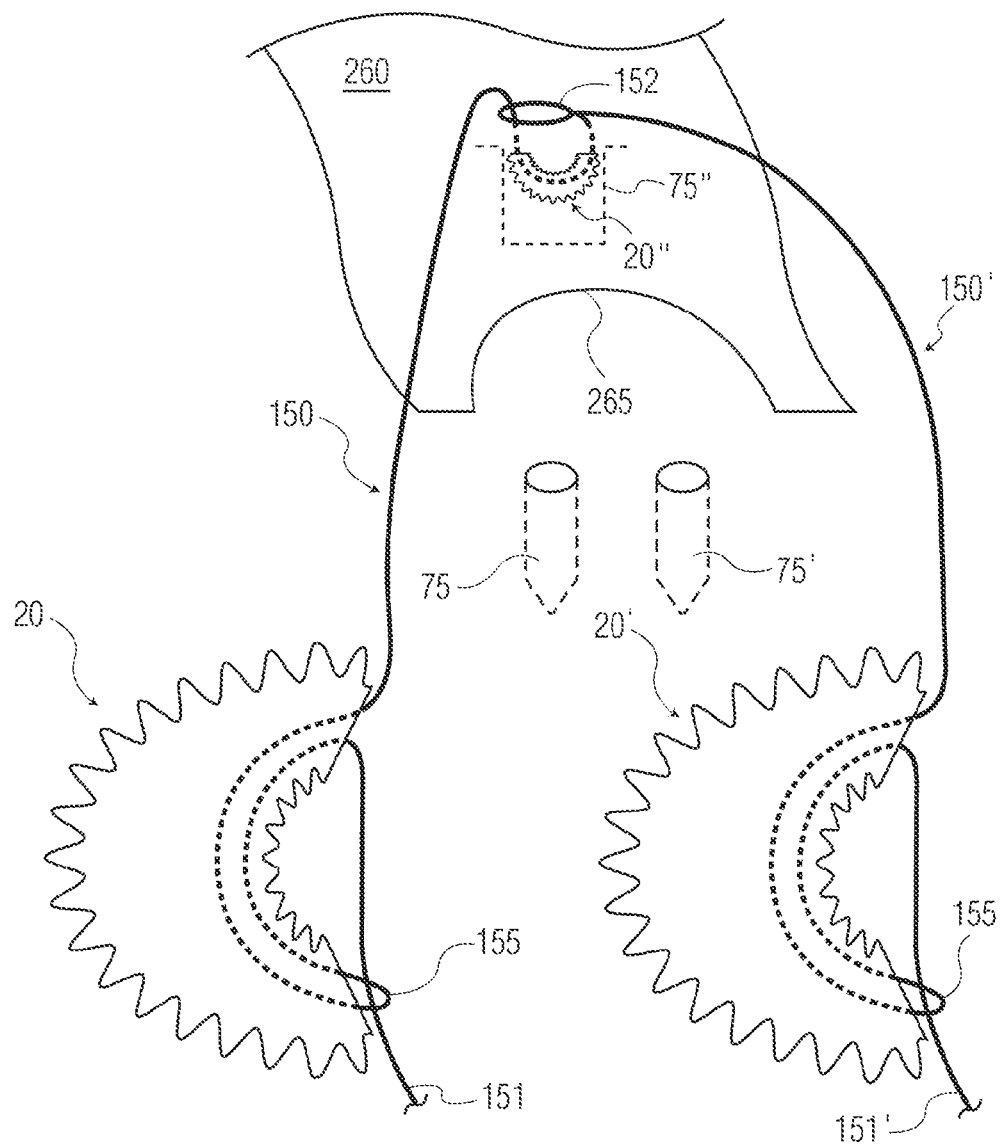

FIG. 12B illustrates an alternative configuration of FIG. 12A in which filament 150 (with two tails 151 and 151') is instead positioned through a third filamentary fixation device 20", positioned in bore hole 75". Bore hole 75" is considered a medial bore hole, which, once the repair is complete will be positioned beneath the rotator cuff tissue, as is known in the art. The third device 20" can be an ICONIX® filamentary device (mentioned above). The addition of the device 20" can allow for the luggage tag configuration of loop 152 and free end 151 to compress the tissue down directly to the bone at the desired hole location 75" which may result in an improved repair.

FIGS. 11A-C illustrate a further embodiment of the present invention including a method of securing tissue. Generally, this method includes steps which are similar to the above-discussed embodiments, though the fixation device has been replaced—such that sleeve 20 has been replaced by a traditional suture or tissue anchor 120. One example of anchor 120 may be a TwinLoop® anchor (Howmedica Osteonics, Mahwah, N.J.), which includes two suture loops 121, 122 for attachment of a filament, and tissue, thereto. Additionally, this embodiment utilizes length of filament 150, though filament 50 may also be used as desired. As illustrated, anchor 120 can be positioned in a bore hole 75 in bone 70 or threaded directly into bone as is known in the art. In an alternative embodiment, the anchor 120 itself may include a U-shaped passage therethrough rather than suture loops 121, 122, such that the filament (and shuttle) can be positioned through the U-shaped passage in a similar manner. For example, if suture loops 121, 122 are removed from the TwinLoop® anchor, the anchor includes such a U-shaped passage which may be used. While either embodiment is envisioned, the embodiment using loops 121, 122 will now be described.

FIG. 11A illustrates the first step, as in FIGS. 4A and 5 above, where filament 150 is directed to and threaded through loop configuration 35 of filamentary shuttle 30, which is positioned through suture loops 121, 122. As with any of the disclosed embodiments, shuttle 130 (and optionally inner filament 40) may also be used. FIG. 11B, similar to FIGS. 6 and 7A, above, illustrate tensioning shuttle ends 31, 32 to pull filament 150 into and through suture loops 121, 122 to form a second loop configuration 155. The shuttle may be withdrawn from the second loop configuration 155 and discarded. Finally, in FIG. 11C, as in FIGS. 8A and 8B, free end 151 is passed through the second loop configuration 155. The free end 151 can continue to be tensioned, as in FIGS. 9A and 9B above, to compress loop configuration 155 and form the aforementioned one-way cleat as to free end 151. Suture loops 121, 122 must be sufficiently small to create the one-way cleat but sufficiently large to allow shuttling of filament 150. Moreover, as with the embodiments discussed above, it is preferred that these various steps be performed through a cannula (as in FIG. 8B) in an arthroscopic manner, such that, for example, the loop configuration 35 and ends 31, 32 of shuttle 30, free end 151, and formed loop configuration 155 are all positioned proximally through the cannula and outside to the operator such that each of these steps can be performed outside of the surgical site. Also, it is envisioned that multiple filaments 50, 150 may be used with a single anchor 120, or multiple anchors as desired.

In another embodiment, the present invention includes a system for the repair of soft tissue including at least one filamentary fixation assembly, at least one instrument for insertion of the filamentary fixation assembly, and a surgical procedure. The surgical procedure may include instructions or protocol for using the filamentary fixation assembly and instrument to repair soft tissue. The protocol may include aspects of any of the above-discussed embodiments, though other variations are also envisioned within the scope of the present invention.

In an associated embodiment, the present invention includes a method of providing instructions or information to practice any of the various methods of performing soft tissue repair described herein. For example, the method may include supplying a surgical protocol, or like document, to provide step-by-step instructions for performing any of the method embodiments of the present invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of securing tissue using a filamentary construct, comprising the steps of:
   obtaining a filamentary sleeve formed of filament and having a length along a longitudinal axis and a pathway there through and a filamentary shuttle positioned at least partially through the pathway;
   obtaining a length of filament having a first free end and a second free end and being in a working relationship with the tissue;
   passing the first free end of the length of filament through the filamentary shuttle to connect the length of the filament to the shuttle;
   pulling at least a portion of the length of filament into the filamentary sleeve;
   continuing to pull at least a portion of the length of filament into and through the sleeve, thereby forming a loop configuration on the length of filament, wherein in this position, the length of filament is folded over itself, forming the loop configuration at one end protruding from the filamentary sleeve and positioning the first and second free ends at the other end protruding from the filamentary sleeve;
   passing the first and second free ends of the length of filament through the loop configuration; and
   tensioning the first and second free ends such that the loop configuration travels towards and into the filamentary sleeve, the length of filament adapted to apply tension to the tissue, and the first and second filament free ends, passed through the loop configuration, are secured within the loop configuration.

2. The method of claim 1, wherein the filamentary shuttle includes an eyelet formed by an inner filament, positioned within an interior passageway of the filamentary shuttle, wherein a portion of the inner filament extends out of the interior passageway and the portion includes the eyelet.

3. The method of claim 1, further comprising, prior to the step of engaging the length of filament with the filamentary shuttle, implanting the filamentary sleeve into a prepared bore hole in a bone and deploying the filamentary sleeve such that the filamentary sleeve is fixedly secured within the bore hole.

4. The method of claim 1, wherein the length of filament is passed around or through the tissue, such that the length of filament includes the two free ends.

5. The method of claim 1, wherein the filamentary sleeve is a braided structure.

6. A method of securing tissue using a filamentary construct, comprising the steps of:
   passing a first end of a length of filament through or around tissue to connect the length of filament to the tissue;
   implanting a filamentary sleeve, formed of filament, into bone; and
   passing at least a portion of the length of filament at least partially through the filamentary sleeve to form a one-way cleat, wherein the one-way cleat is formed by continuing to pull at least a portion of the length of filament into and through the sleeve, thereby forming a loop configuration on the length of filament extending from the filament sleeve, wherein in this position, the length of filament is folded over itself, forming the loop configuration at one end extending from the filament sleeve and at least one filament free end at the other end protruding from the sleeve; passing the at least one free end of the length of filament through the loop configuration; and tensioning the at least one free end such that the loop configuration travels towards and into the filamentary sleeve, the length of filament adapted to apply tension to the tissue, such tension applied only after implanting the filamentary sleeve and forming the one way cleat, and the at least one filament free end, passed through the loop configuration, is secured within the loop configuration.

7. The method of claim 6, comprising the additional step of, upon implanting the sleeve in bone, deploying the sleeve to fixedly secure the sleeve relative to the bone.

8. The method of claim 6, wherein the filamentary sleeve includes a filamentary shuttle and the step of passing the portion of the length of filament includes engaging the portion of the length of filament with the filamentary shuttle and pulling the portion of the length of filament through the filamentary sleeve.

9. The method of claim 6, wherein the filamentary sleeve is a woven structure.

* * * * *